United States Patent
Michelson et al.

(10) Patent No.: US 6,445,955 B1
(45) Date of Patent: Sep. 3, 2002

(54) MINIATURE WIRELESS TRANSCUTANEOUS ELECTRICAL NEURO OR MUSCULAR-STIMULATION UNIT

(76) Inventors: Stephen A. Michelson, 4817 NW. 65th Ave., Lauderhill, FL (US) 33319; Jeffrey S. Mannheimer, 11 Ardsley Ct., Newton, PA (US) 18940; Robert Leon, 3525 SW. 111th Ave., Miami, FL (US) 33165; Osvaldo D. Romero, 5782 SW. 16th St., Miami, FL (US) 33155; Jerald A. Selevan, 5701 SW. 74th Ave., Miami, FL (US) 33143

( * ) Notice: Subject to any disclaimer, the term of this patent is extended or adjusted under 35 U.S.C. 154(b) by 0 days.

(21) Appl. No.: 09/350,426

(22) Filed: Jul. 8, 1999

(51) Int. Cl.[7] ................................................ A61N 1/08
(52) U.S. Cl. ........................... 607/46; 607/72; 607/2; 607/59
(58) Field of Search ............................. 607/30, 46, 72, 607/74, 68, 60, 59, 50, 2

(56) References Cited

U.S. PATENT DOCUMENTS

| | | | |
|---|---|---|---|
| 4,699,143 A | 10/1987 | Dufresne et al. | |
| 4,759,368 A | 7/1988 | Spanton et al. | |
| 4,832,032 A * | 5/1989 | Schneider | 128/419 |
| 4,989,605 A | 2/1991 | Rossen | |
| 5,041,974 A * | 8/1991 | Walker et al. | 364/413.27 |
| 5,183,041 A | 2/1993 | Toriu et al. | |
| 5,304,207 A | 4/1994 | Stromer | |
| 5,350,414 A * | 9/1994 | Kolen | 607/62 |
| 5,354,320 A | 10/1994 | Schaldach et al. | |
| 5,374,283 A | 12/1994 | Flick | |
| 5,387,231 A | 2/1995 | Sporer | |
| 5,395,398 A * | 3/1995 | Rogozinski | 607/50 |
| 5,397,338 A | 3/1995 | Grey et al. | |
| 5,476,481 A | 12/1995 | Schöndorf | |
| 5,487,759 A * | 1/1996 | Bastyr et al. | 607/149 |
| 5,514,165 A | 5/1996 | Malaugh et al. | |
| 5,549,656 A | 8/1996 | Reiss | |
| 5,573,552 A | 11/1996 | Hansjurgens et al. | |
| 5,578,060 A | 11/1996 | Pohl et al. | |
| 5,584,863 A | 12/1996 | Rauch et al. | |
| 5,593,427 A | 1/1997 | Gliner et al. | |
| 5,601,612 A | 2/1997 | Gliner et al. | |
| 5,607,454 A | 3/1997 | Cameron et al. | |
| 5,620,470 A | 4/1997 | Gliner et al. | |
| 5,674,261 A * | 10/1997 | Smith | 607/46 |
| 6,029,090 A * | 2/2000 | Herbst | 607/66 |

* cited by examiner

*Primary Examiner*—Kennedy Schaetzle
(74) *Attorney, Agent, or Firm*—Lott & Friedland, P.A.

(57) ABSTRACT

A miniature wireless transcutaneous electrical neuro or muscular stimulation unit. The unit has a housing attached to a plurality of electrodes. An electronics module containing an electrical circuit is contained within the housing and provides a sequence of monophasic or biphasic pulses to a patient's pain site via the electrodes. The electrodes can be disposable and come in a variety of shapes and sizes. The patient may select and control the intensity and the frequency of the pulses by choosing one of several TENS and microcurrent waveforms, as well as the orientation and quantity of the electrodes. The means for supplying power to the electronics module can be integrated with the electrodes in one detachable and disposable assembly. A worn-remote controller can send transmission signals to a receiver within the electronic module thereby allowing the patient to program specific units placed on the patient's body to perform operations in a specified series of waveforms. The electrodes may be embedded in a splint, bandage, brace or cast, where wires or flex-circuit material connect the electrodes to the unit. The electrodes can be arranged in a grid-like manner to allow for programming of a specific firing order which provides for greater therapeutic effect to a pain site, and may also be embedded in adhesive strips, similar to a conventional Band-Aid.

47 Claims, 34 Drawing Sheets

MINIATURE WIRELESS TRANSCUTANEOUS ELECTRICAL NEURO OR MUSCULAR-STIMULATION UNIT

TECHNICAL FIELD

The invention relates generally to transcutaneous electrical neuro-stimulation (TENS) units and this invention particularly relates to a miniaturized wireless TENS unit capable of being pre-programmed to achieve a variety of waveforms, with or without the use of a remote controller means, each with unique features capable of masking pain or promoting functional restoration in a user's body.

BACKGROUND OF THE INVENTION

TENS devices have been traditionally prescribed in the medical industry for chronic pain. While patients experiencing acute pain are prescribed anti-inflammatories and narcotic agents, the treatment of chronic pain, usually defined as unrelieved pain for at least 30 days, has usually been dealt with via TENS-related prescriptions. However, TENS devices have been shown to provide rapid and effective relief for acute pain without side effects or the possibility of addiction. TENS does not utilize anesthesia or narcosis. Patients remain awake, alert and functional, and retain the protective qualities of increased pain perception.

TENS is commonly used for acute pain management by physical therapists in comprehensive rehabilitation programs in conjunction with other treatments. TENS devices are usually large as well as being complex, expensive and require lead wires running to each electrode, making them difficult for use at home, at work or at play.

Consequently there is a need in the art for a miniaturized, wireless TENS device that can be utilized by the patient without the embarrassment of unsightly wires protruding through clothing, and that can be placed on a variety of sites on the patient's body, virtually unseen, and which can be controlled by a controller means to transmit pulses at different intensities and frequencies adaptable to the patient's particular physical malady.

Previous attempts have been made to design improved electro-therapy devices, certain features of which are generally described in U.S. Pat. No. 5,620,470 to Gliner et al.; U.S. Pat. No. 5,607,454 to Cameron et al.; U.S. Pat. No. 5,601,612 to Gliner et al.; U.S. Pat. No. 5,593,427 to Gliner et al.; U.S. Pat. No. 5,584,863 to Rauch et al.; U.S. Pat. No. 5,578,060 to Pohl et al.; U.S. Pat. No. 5,573,552 to Hansjurgens; U.S. Pat. No. 5,549,656 to Reiss; U.S. Pat. No. 5,514,165 to Malaugh et al.; U.S. Pat. No. 5,476,481 to Schöndorf; U.S. Pat. No. 5,387,231 to Sporer,; U.S. Pat. No. 5,397,338 to Grey et al.,; U.S. Pat. No. 5,374,283 to Flick,; U.S. Pat. No. 5,354,320 to Schaldach et al.; U.S. Pat. No. 5,304,207 to Stromer; U.S. Pat. No. 5,183,041 to Toriu et al.; U.S. Pat. No. 4,989,605 to Rossen; U.S. Pat. No. 4,759,368 to Spanton et al.; U.S. Pat. No. 4,699,143 to Dufresne et al.; and U.S. Pat. No. 4,398,545 to Wilson, all of which are incorporated herein by reference. However, none of these references, either alone or in combination with others, describes a miniature, wireless transcutaneous neuro stimulation device with a remote controlled configuration that has pre-programmable waveform modes and includes a unique detachable electrode-battery assembly. What is needed is a miniature, wireless TENS-related device that can easily be programmed by the user, with or without the use of a remote controller, to provide a variety of waveforms at various programmable intensities to a number of pain sites on the user's body, and which can be easily adaptable for use with splints, braces and bandages. The present invention satisfies this need.

SUMMARY OF THE INVENTION

Generally, the present invention provides a miniature wireless transcutaneous electrical neuro or muscular-stimulation unit including a housing; a plurality of electrodes attached to the housing; an electronics module located within the housing and comprising an electrical circuit which provides a biphasic or monophasic sequence of pulses to the electrodes, wherein the sequence of pulses form a plurality of pre-programmable waveforms available for specific clinical needs; means to restrict the waveforms available to those appropriate for the electrode and treatment through a series of one or more protrusions within the housing, wherein the protrusions interface with the electronics module to determine the waveform to be used; means for allowing a user to select and control specific waveforms and intensities of the waveforms; means to identify the specific waveform chosen, its intensity and its duration; and means for supplying power to the electronics module wherein the means for supplying power is integrated with the electrodes in one assembly.

In an alternate embodiment the means for supplying power to the electronics module is a plurality of batteries.

An alternate embodiment of the present invention provides that the batteries are replaceable or rechargeable.

In an alternate version, the identifying means is an LCD digital readout display.

In an alternate embodiment, the means for allowing the user to select and control specific waveforms and intensities of waveforms is through a series of input devices controlling an LCD digital readout display which allows the user to vary the intensity of the waveforms.

In an alternate form, the means for allowing the user to select and control specific waveforms and intensities of waveforms comprises a removable tether having a first and second end wherein the first end is affixed to the electrode-battery assembly and the second end is affixed to the miniature wireless transcutaneous electrical neuro or muscular-stimulation unit.

In an alternate embodiment, the electrodes are disposable.

An alternate embodiment of the present invention provides that the electronics module be disposable.

In an alternate embodiment, the electronics module is detachable and is able to be snapped into and out of each miniature wireless transcutaneous electrical neuro or muscular-stimulation unit.

In an alternate form, the plurality of electrodes have varying shapes and sizes and can be affixed directly to a site or other area requiring electrical neuro or muscular-stimulation anywhere on the user's body, the electrodes are positioned at a specified distance from the electronics module wherein the electrodes are swivel or fixed electrodes which allow for optimal placement of the electrodes at the pain site or the area requiring electrical neuro or muscular-stimulation.

In an alternate embodiment, the plurality of waveforms are comprised of but not limited to, a conventional-low mode and a conventional-high mode, a modulation-low mode and a modulation-high mode, an acupuncture-like low mode and an acupuncture-like high mode, a microcurrent mode, a burst mode and a cycling mode wherein the conventional-low mode supplies to the plurality of electrodes biphasic or monophasic pulses of about 0–60 milliamperes at a frequency of about 100 Hz having a pulse width of about 75 microseconds, the conventional-high mode supplies to the electrodes biphasic or monophasic pulses of about 0–100 milliamperes at a frequency of about 100 Hz having a pulse width of about 125 microseconds, the modulation-low mode supplies to the electrodes biphasic or monophasic pulses of about 0–60 milliamperes at a frequency of about 50–100 Hz having a pulse width of about 75–100 microseconds, the modulation-high mode supplies to the electrodes biphasic or monophasic pulses of about 0–100 milliamperes at a frequency of about 75–100 Hz having a pulse width of about 100–125 microseconds, the acupuncture-like low mode supplies to the plurality of electrodes biphasic pulses of about 0–60 milliamperes at a frequency of about 1 Hz having a pulse width of about 75 microseconds, the acupuncture-like high mode supplies to the electrodes biphasic pulses of about 0–100 milliamperes at a frequency of about 2 Hz having a pulse width of about 125 microseconds, the microcurrent mode supplies to the plurality of electrodes biphasic pulse of about 0–100 microamperes at a frequency of about 0.3–100 Hz, the burst mode supplies to the plurality of electrodes biphasic or monophasic pulses of about 0–100 milliamperes at a frequency of about 100 Hz having a pulse width of about 75 microseconds for a duration of three seconds on and three seconds off, and the cycling mode allows the user to program two or more modes into an individualized program.

In an alternate form, the plurality of waveforms are comprised of but not limited to, three unique muscle stimulation modes, a conventional mode, a modulation mode and three alternative cycling modes, wherein the first muscle stimulation mode supplies to the plurality of electrodes biphasic or monophasic pulses typically of about 0–100 milliamperes at a frequency of about 45 Hz at a pulse width of about 300 microseconds for approximately 5 minutes on and 5 minutes off, wherein the second muscle stimulation mode supplies to the plurality of electrodes biphasic or monophasic pulses typically of about 0–100 milliamperes at a frequency of about 45 Hz at a pulse width of about 300 microseconds for approximately 10 minutes on and 10 minutes off, the third muscle stimulation mode supplies to the plurality of electrodes biphasic or monophasic pulses typically of about 0–100 milliamperes at a frequency of about 45 Hz at a pulse width of about 300 microseconds for approximately 10 minutes on and 50 minutes off, the conventional mode supplies to the plurality of electrodes biphasic or monophasic pulses typically of about 0–100 milliamperes at a frequency of about 125 Hz at a pulse width of about 125 microseconds, the modulation mode supplies to the plurality of electrodes biphasic or monophasic pulses typically of about 0–100 milliamperes at a frequency of about 75–100 Hz at a pulse width of about 100–125 microseconds, the first alternative cycling mode supplies to the plurality of electrodes a sequence of biphasic or monophasic pulses comprised of the modulation mode for about 3 minutes followed by the first muscle stimulation mode for about 9 minutes, followed by the modulation for about 3 minutes, the second alternative cycling mode supplies to the plurality of electrodes a sequence of biphasic or monophasic pulses comprised of the modulation mode for about 3 minutes followed by the first muscle stimulation mode for about 9 minutes, followed by the modulation mode for about 3 minutes, and the third alternative cycling mode supplies to the plurality of electrodes a sequence of biphasic or monophasic pulses comprised of the modulation mode for about 3 minutes followed by the third muscle stimulation mode for about 9 minutes, followed by the modulation mode for about 3 minutes.

In an alternate embodiment of the present invention, an electrode-battery assembly is used in a miniature wireless transcutaneous electrical neuro or muscular-stimulation unit comprising a plurality of electrodes each having an internal and external side, a plurality of batteries each having a positive and negative pole, a flexible non-conductive carrier with a hydrogel which carries current to a pain site or other area on a user's body via the electrodes, conductive film comprised of three current carrier runners wherein two of the runners are in direct contact with each of the positive and negative poles of the battery and a third said runner is in direct contact with the hydrogel, and a mechanical battery clip which secures the runners to the positive and negative battery poles.

In an alternate form, the electrode-battery assembly is disposable and can be replaced upon depletion of the battery.

In an alternate embodiment, the conductive film of the electrode-battery assembly is comprised of a silver alloy film or some other flexible low impedance material.

In another form, the external side of the electrode is covered by a molded cover comprised of a cosmetically appealing molded foam or elastomer.

In an alternate embodiment, a method of relieving acute or chronic body pain or muscle dysfunction requiring electrical neuro or muscular-stimulation on a user's body using the miniature wireless transcutaneous electrical neuro or muscular-stimulation device described herein comprises the steps of affixing the plurality of disposable electrodes to a treatment site or other area requiring electrical neuro or muscular-stimulation on a user's body, applying biphasic or monophasic sequence of pulses to the electrodes via an electrical circuit, providing a means for the user to select and control the plurality of waveforms and intensity of waveforms, providing a means for the user to identify the waveform, its intensity and its duration, and providing a means for supplying power to the electronics module wherein the means for supplying power is integrated with the electrodes in one detachable assembly.

In an alternate form, the miniature wireless transcutaneous electrical neuro or muscular-stimulation unit further comprises a transmitting device which includes a time function, a carrier signal capable of sending in a digital format, a means of identifying individual receivers, a synchronizing pulse, a means for setting the waveform mode, the intensity and the time duration, individually, of multiple remote electrode assemblies, a controller means capable of being worn on a comfortable site on the user's body wherein the controller means sends transmission signals to the miniature wireless transcutaneous electrical neuro-stimulation unit by a communication means, and the electronics module further comprises a receiver capable of receiving and decoding signals from the transmitting device.

An alternate embodiment provides that the communication means is achieved by a capacitive coupling comprised of a plurality of conductive plates or transducers placed near the surface of the user's skin wherein one of the conductive plates or transducers resides in the controller means and the other conductive plate or transducer resides in the miniature wireless transcutaneous electrical neuro or muscular-stimulation unit, using the user's body as a conductive medium to transmit the transmission signals.

In an alternate form of the present invention, the controller means transmits signals between 20–500 kHz from the controller means through the user's body to the transcutaneous electrical neuro-stimulation unit.

In an alternate embodiment, the communication means is achieved by over-the-air RF transmission comprised of a plurality of antennas with transmission signals between 40 kHz to 915 MHz.

In an alternate form, the transmission signals are synchronized to the miniature wireless transcutaneous electrical neuro or muscular-stimulation unit's monophasic or biphasic sequence of pulses to avoid interference of transmission signals with monophasic or biphasic sequence of pulses.

An alternate embodiment of the present invention provides for a means of synchronizing the electrodes such that their polarities are 180 degrees out of phase causing electrons to be exchanged between the electrodes.

In an alternate form, the controller means is worn on the user's wrist.

In an alternate version of the present invention, the electronic module is a remote module with display means which allows the remote module to be identified by the controller means and which sets a software address thereby allowing the controller means to send transmissions signals to an identifiable remote module.

In an alternate embodiment, the miniaturized wireless transcutaneous electrical neuro or muscular-stimulation unit further comprises a plurality of post-surgical incisional electrodes, a standard splint, bandage, manufactured brace, or cast comprised of multiple layers wherein the splint, bandage, brace or cast is embedded with non-visible wires or flex-circuit material, the electrodes are embedded in the splint, bandage, brace, or cast, the wires or flex-circuit material provide for connection between the plurality of electrodes and disposable miniaturized transcutaneous electrical neuro-or muscular stimulation unit, and the plurality of electrodes are arranged in a grid-like manner to allow for programming of a specific firing order which can provide for greater therapeutic effect to the pain site.

In another embodiment, the miniature wireless transcutaneous electrical neuro or muscular-stimulation unit further comprises a gauze pad having an antibacterial agent positioned substantially adjacent to and substantially beneath said electronics module, and a plurality of adhesive strips in which the plurality of electrodes are embedded.

In an alternate form, the plurality of waveforms are comprised of but not limited to, a conventional of modulation low mode and a microcurrent mode wherein the conventional-low mode or the modulation-low mode supplies to the plurality of electrodes biphasic or monophasic pulses of about 0–30 milliamperes at a frequency of about 80–100 Hz having a pulse width of about 75 microseconds and the micro current mode supplies to the plurality of electrodes the biphasic pulse of about 0.3–100 Hz.

DETAILED DESCRIPTION OF THE PREFERRED EMBODIMENT

Figure 1:
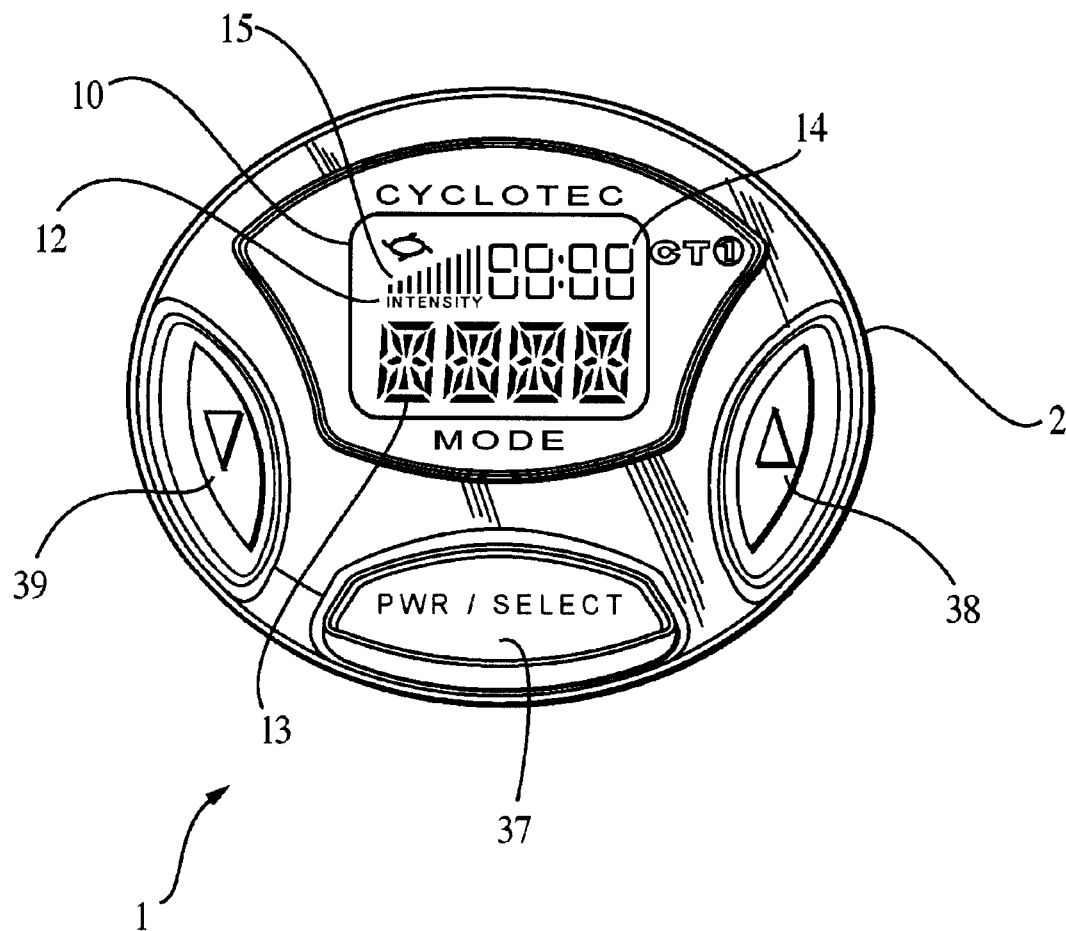
FIG. 1 shows an overhead view of a miniature wireless transcutaneous electrical neuro or muscular-stimulation unit 1.
Figure 2:
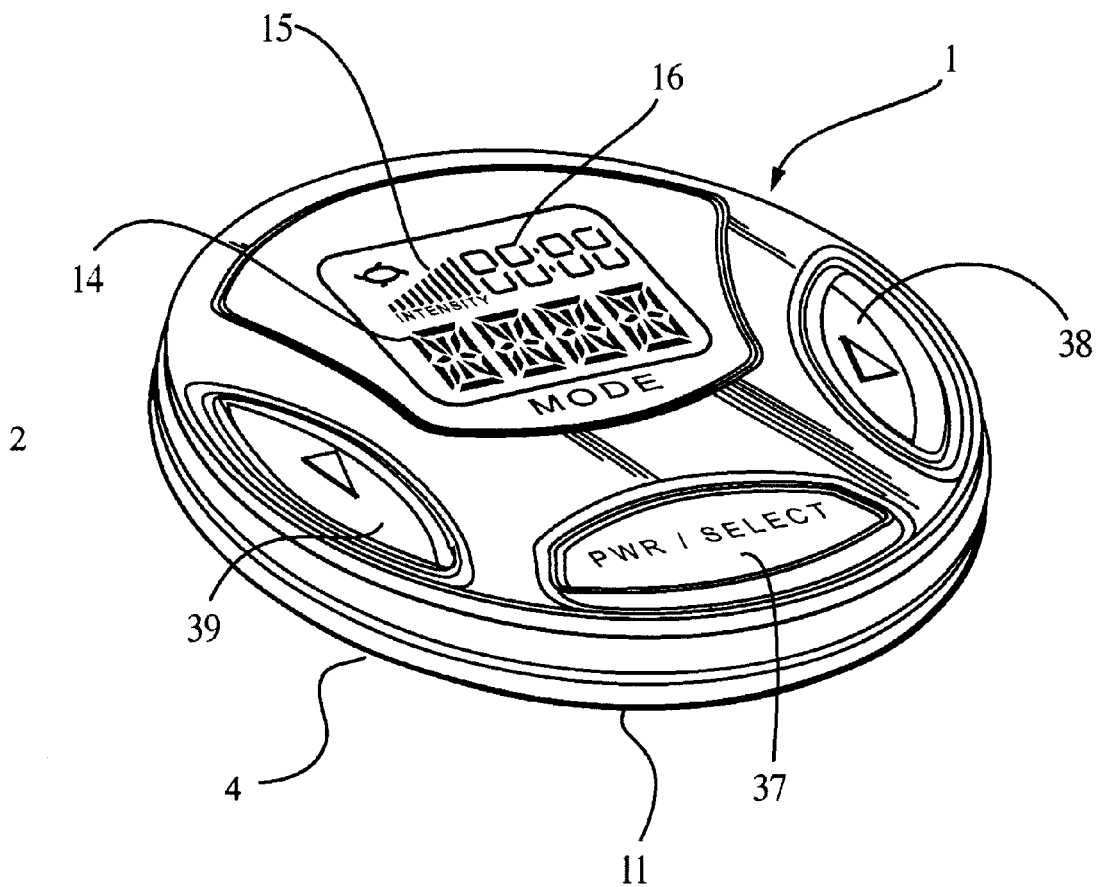
FIG. 2 shows a perspective view of a miniature wireless transcutaneous electrical neuro or muscular-stimulation unit 1.

Turning now to the drawings, in which like numerals indicate like elements throughout the several views, FIG. 1 and FIG. 2 represent the present invention as a water resistant miniature wireless transcutaneous electrical neuro or muscular-stimulation unit 1 comprised of a housing 2 having a front portion 3 and a rear portion 4. The housing 2 which is made of an FDA approved thermoplastic material, has dimensions of approximately 1.5"×1.5"×0.3" and weighs about 4 oz. It is compatible with all versions of electrode/battery assemblies 18 as well as various industry-standard electrodes. 5

Figure 3:
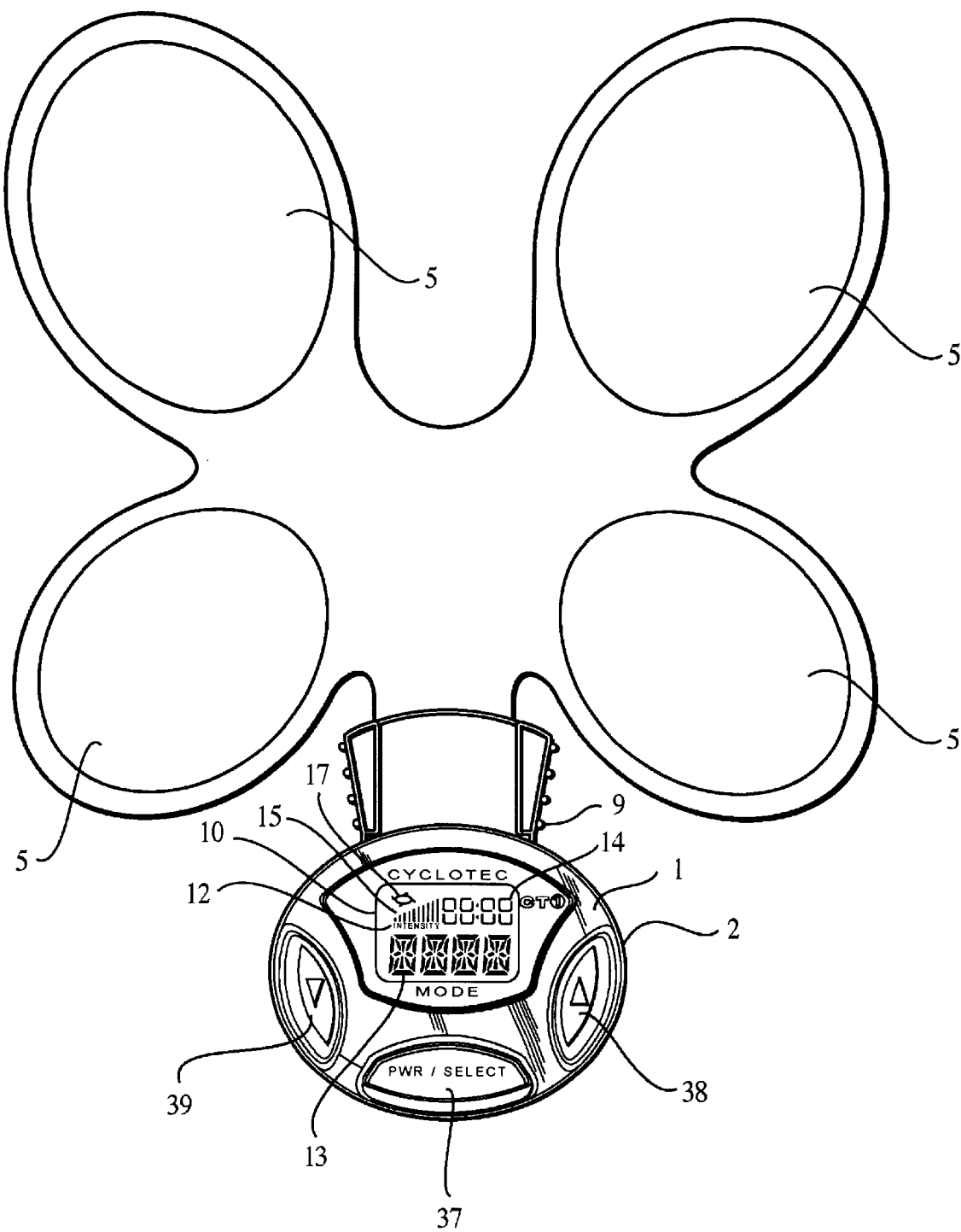
FIG. 3 shows an overhead view of the electrodes 5 and housing 2.
Figure 4A:
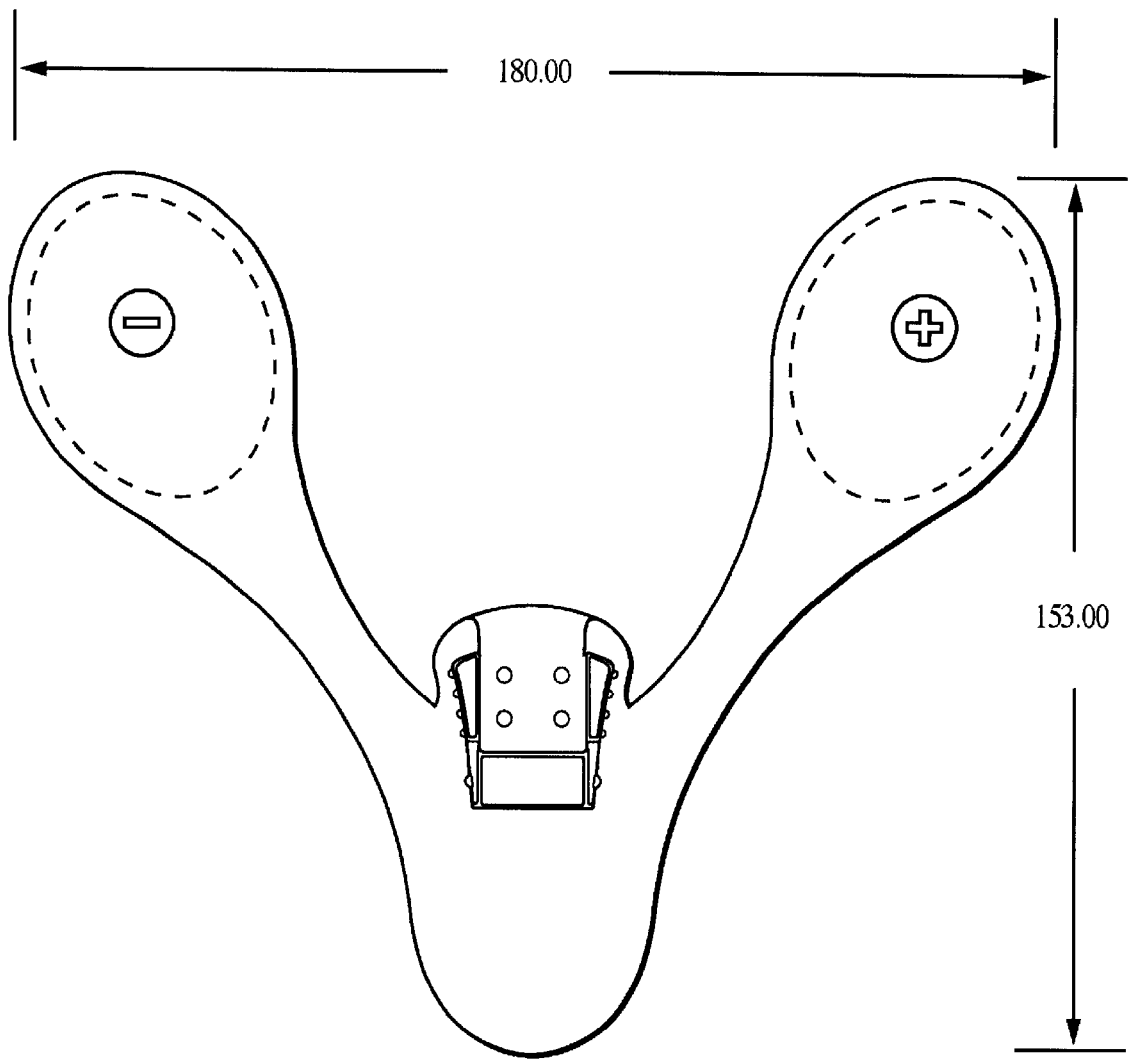
FIGS. 4a–l shows overhead views of several configurations of electrodes 5.
Figure 4B:
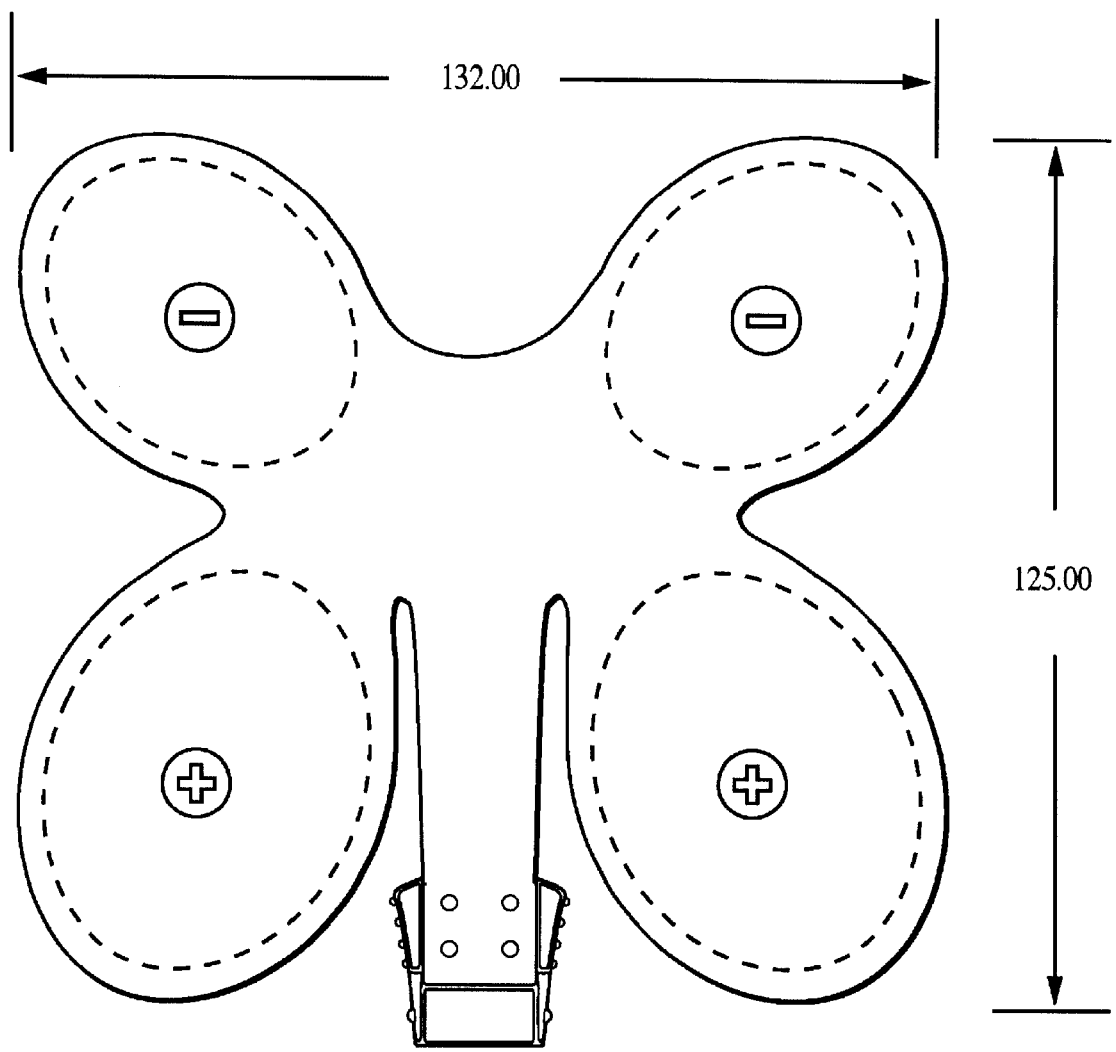
Figure 4C:
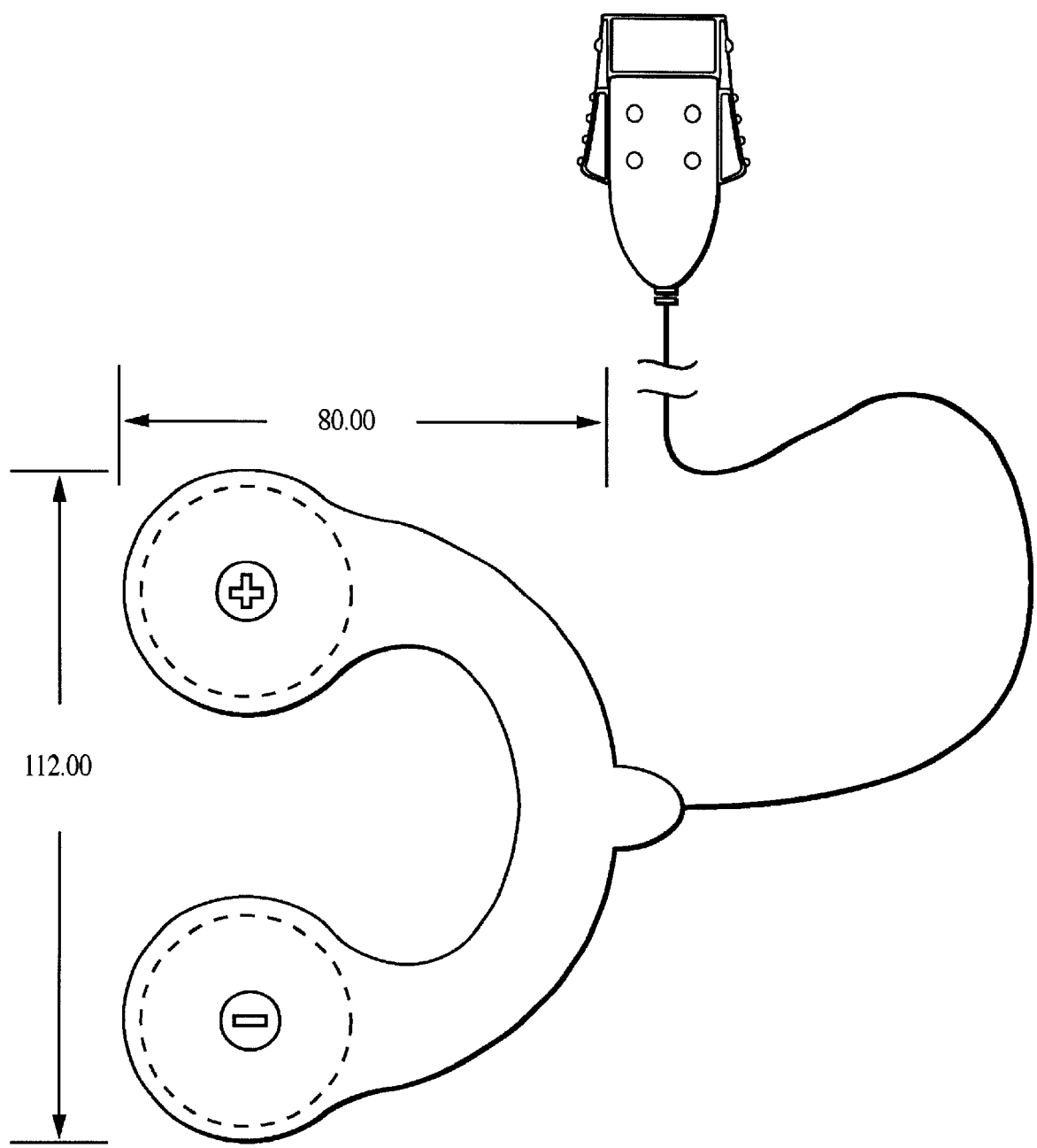
Figure 4D:
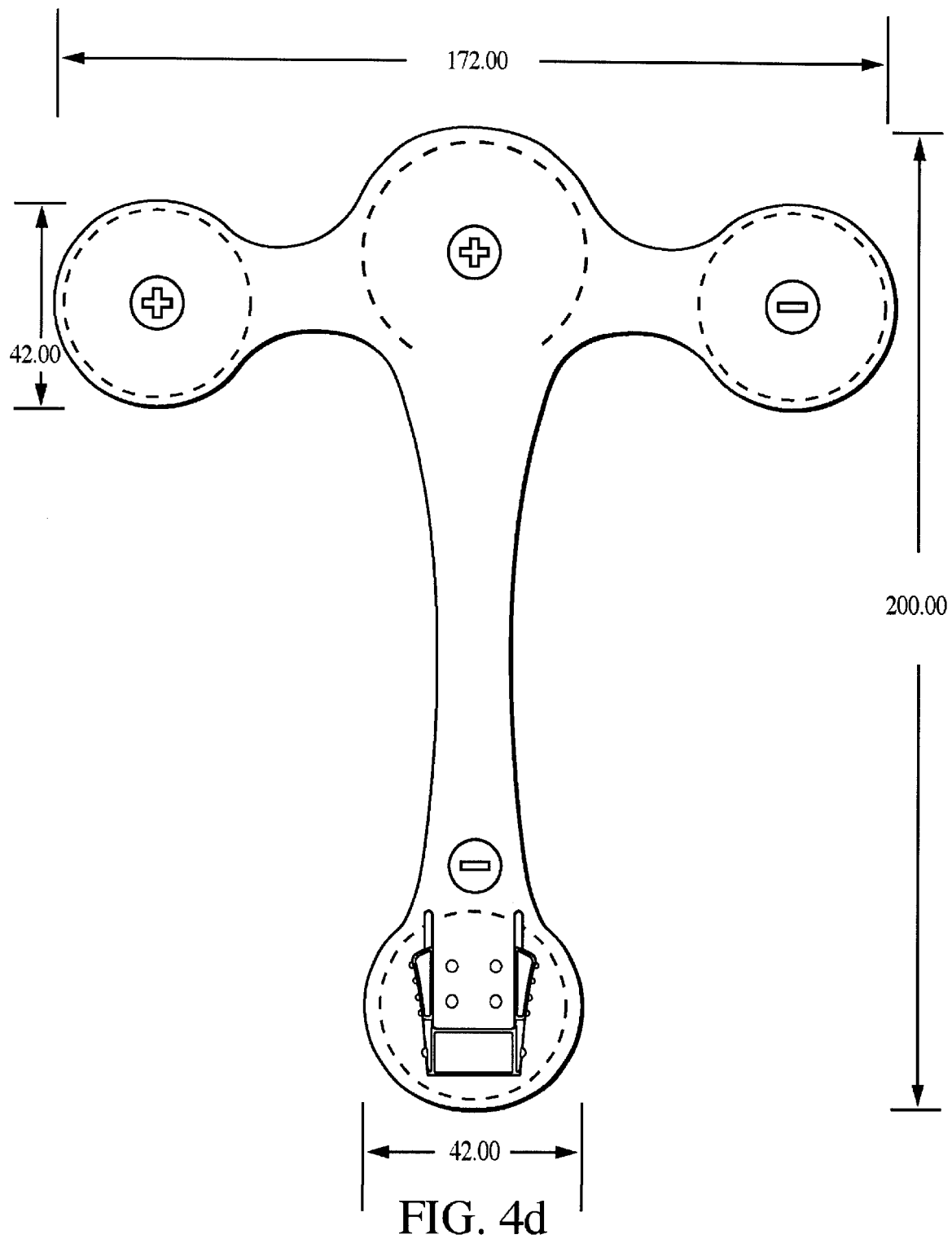
Figure 4E:
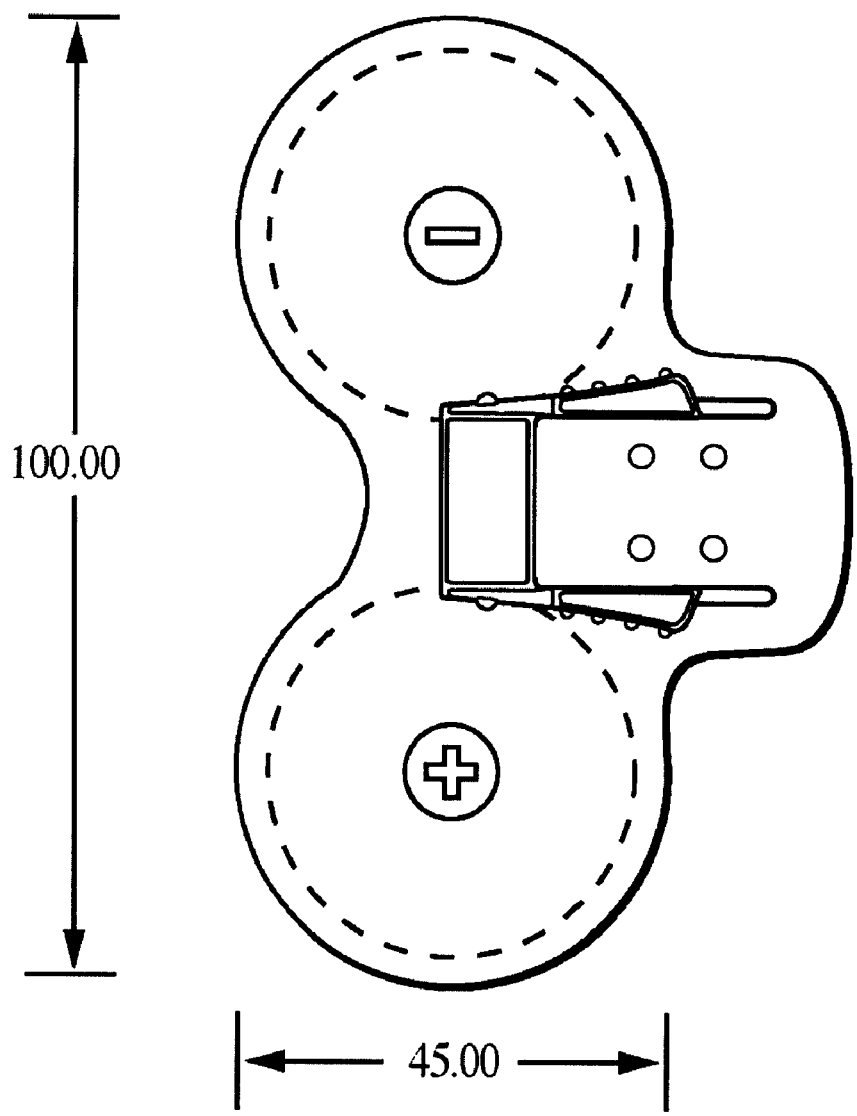
Figure 4F:
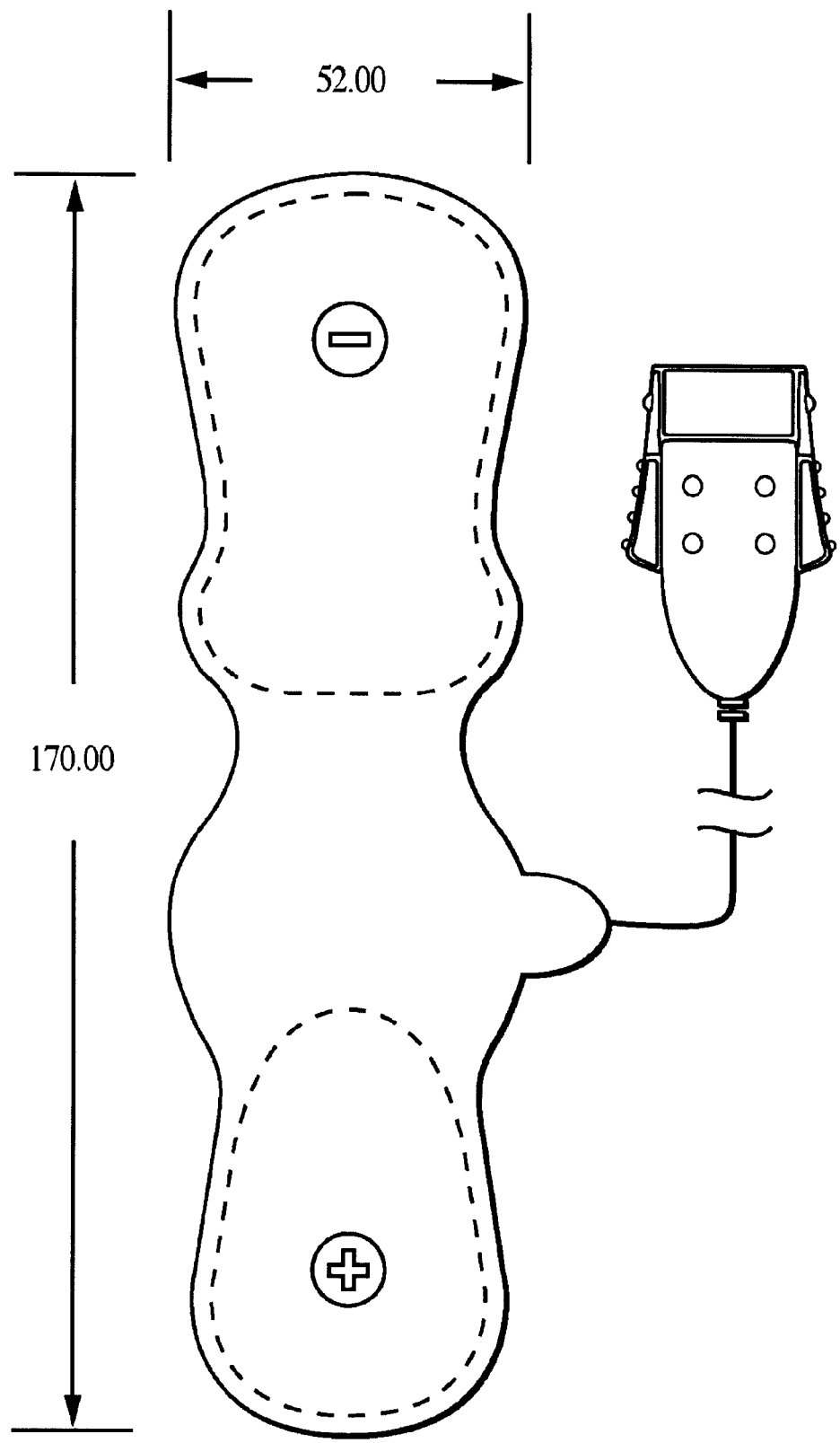
Figure 4G:
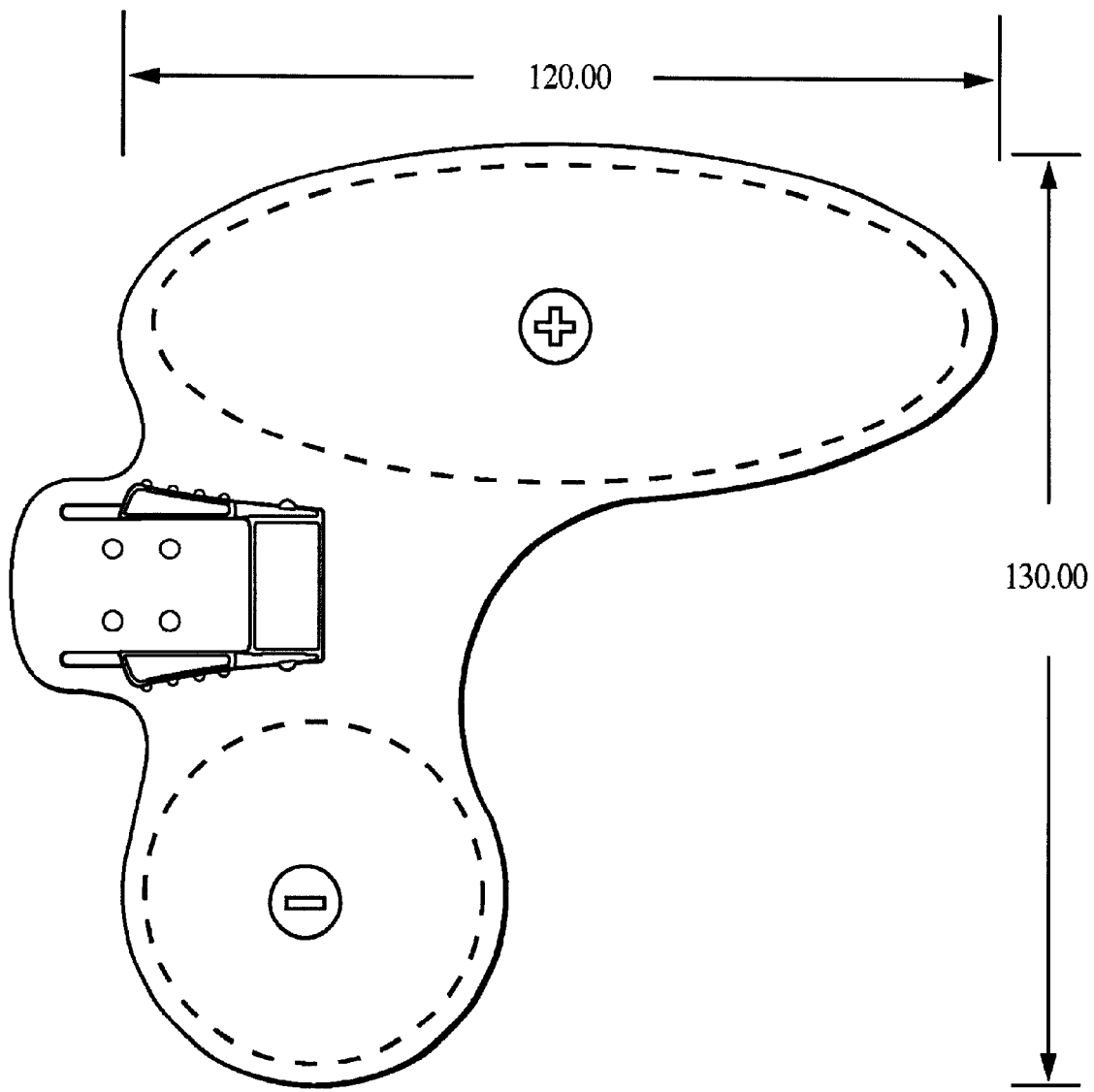
Figure 4H:
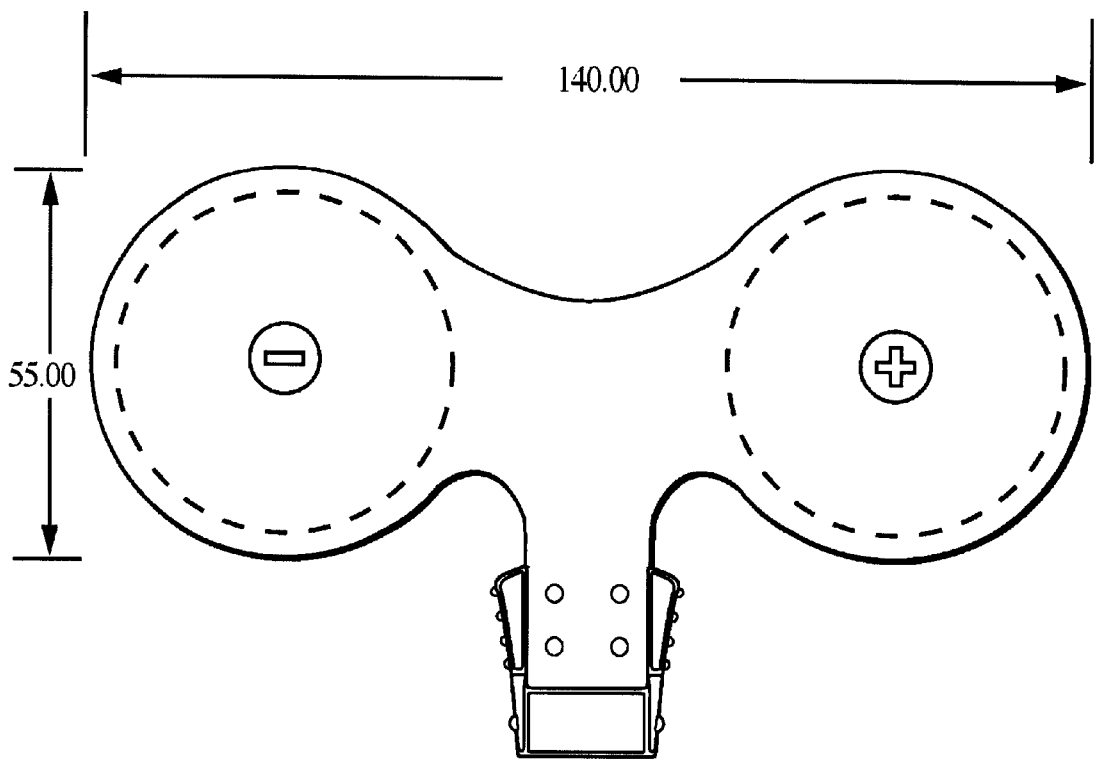
Figure 4I:
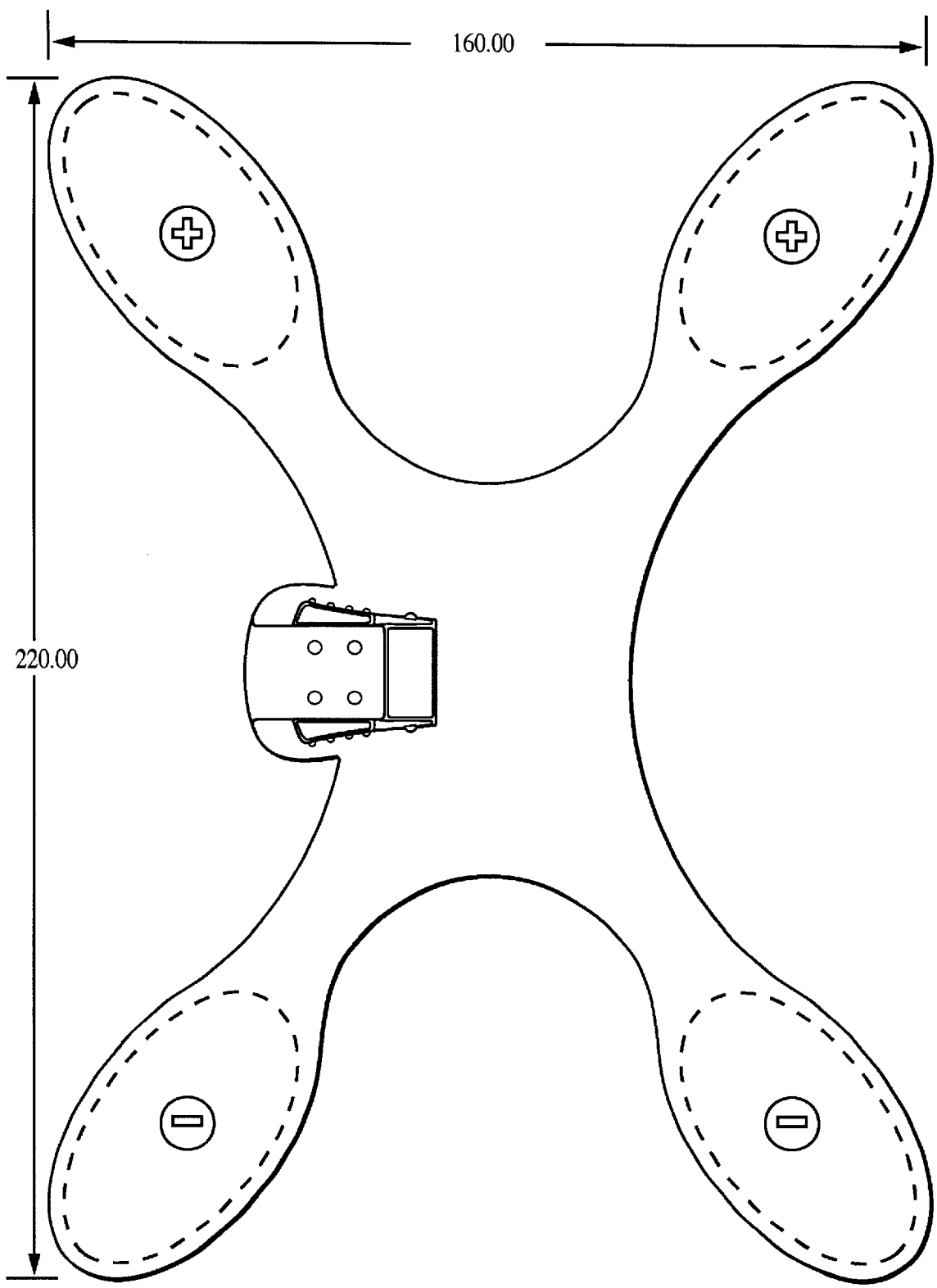
Figure 4J:
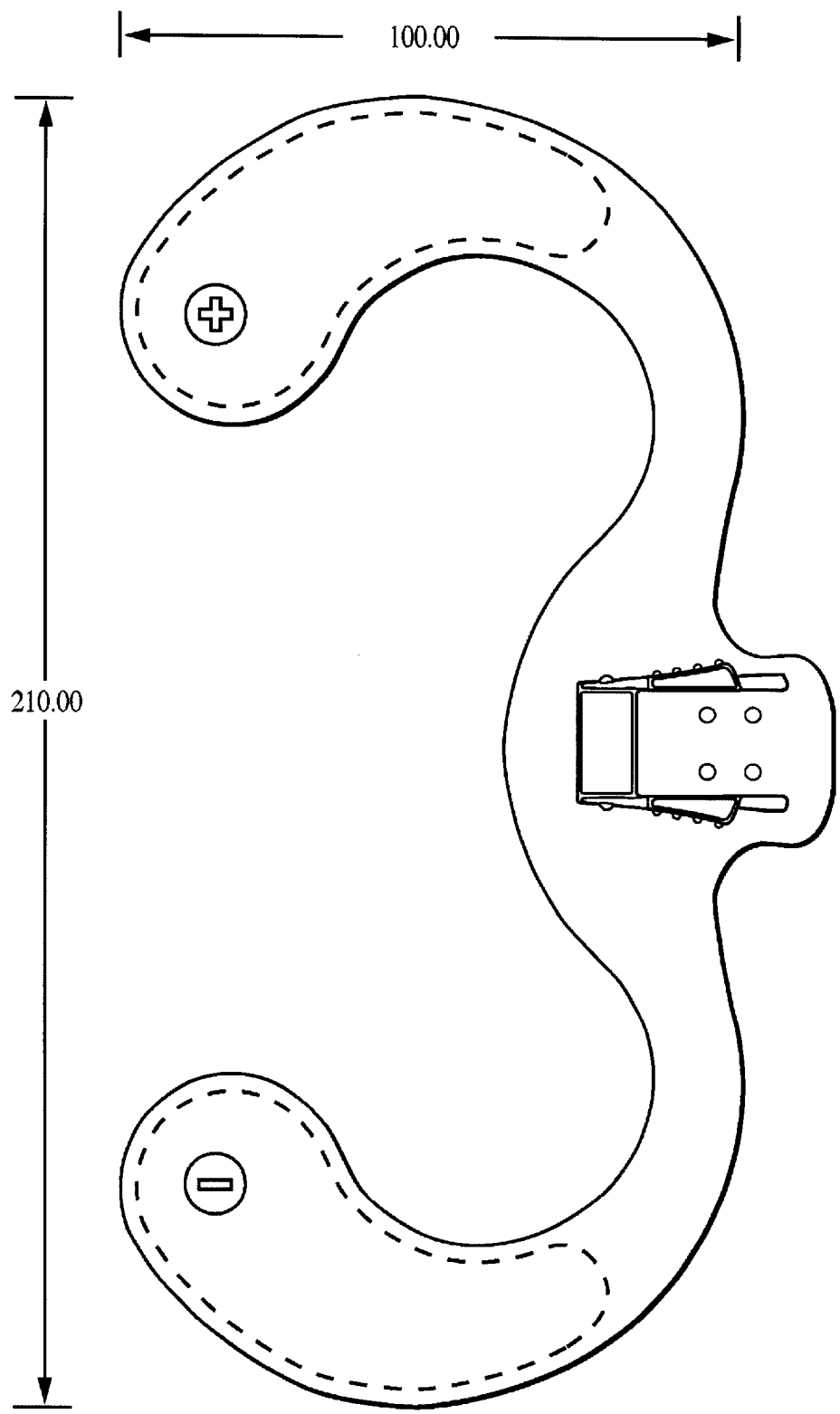
Figure 4K:
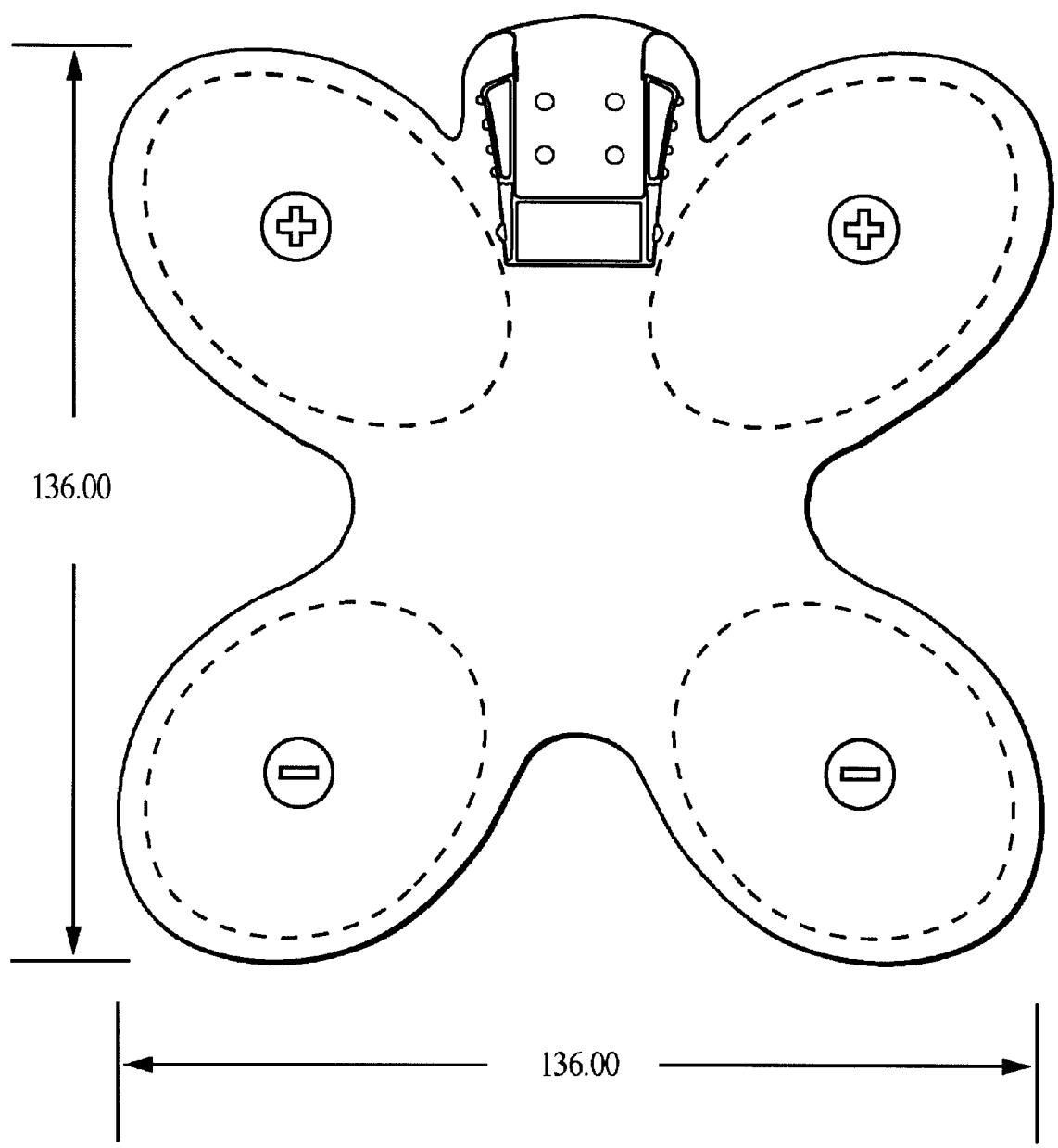
Figure 4L:
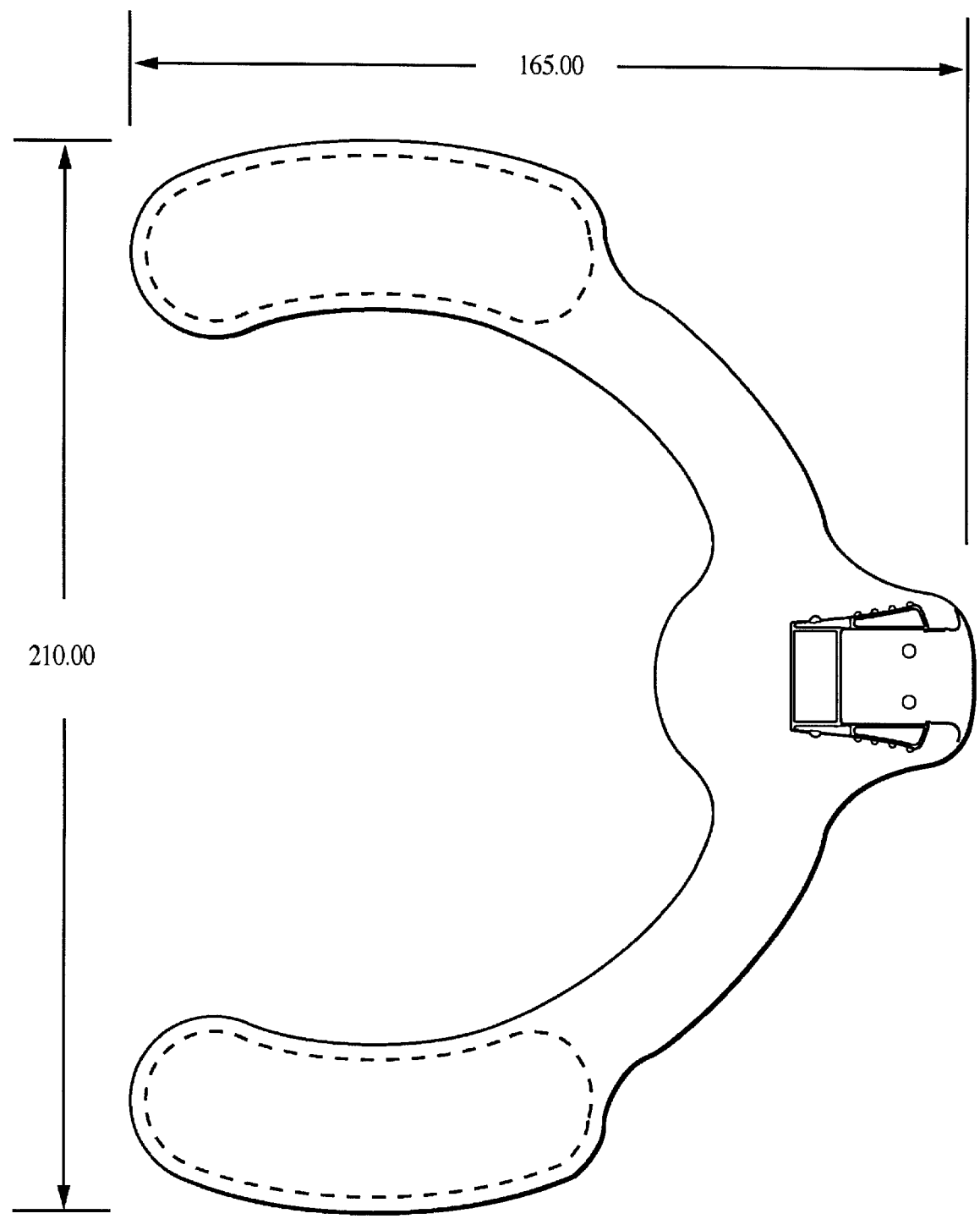
Figure 5:
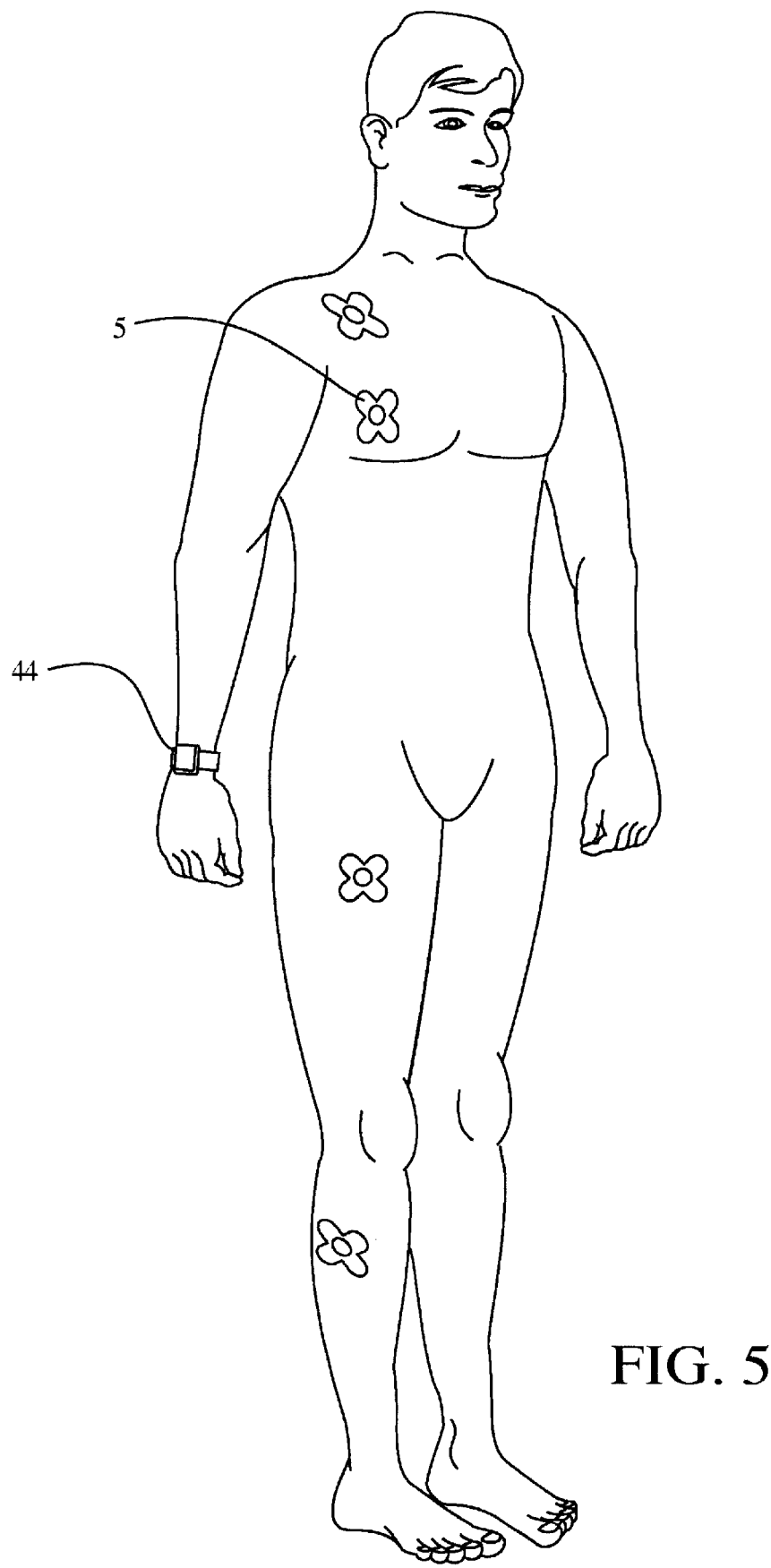
FIG. 5 shows a perspective view of several miniature wireless transcutaneous electrical neuro or muscular-stimulation units 1 placed at various pain sites on a user's body.
Figure 6:
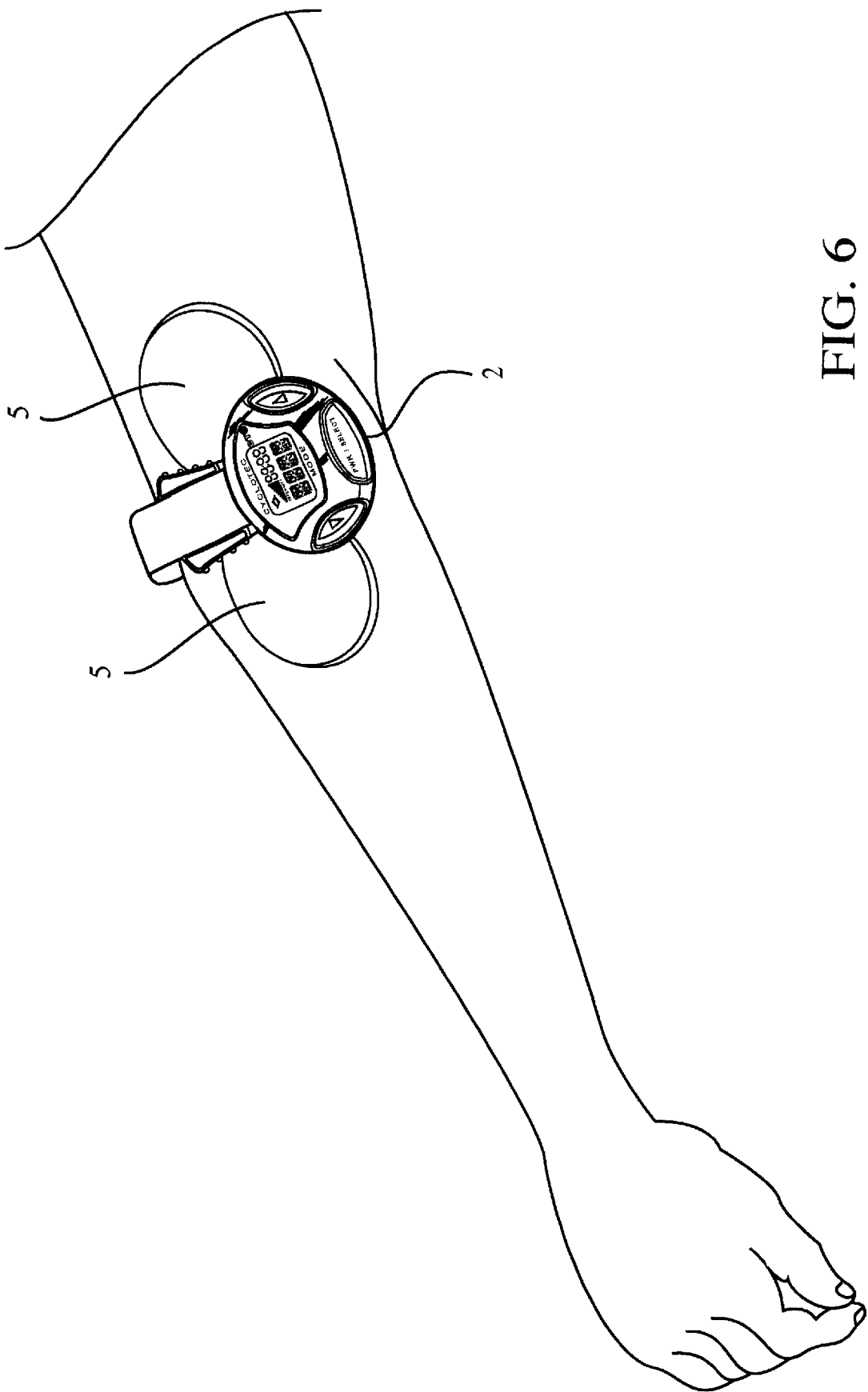
FIG. 6 shows an overhead view of a housing 2 and electrodes 5 applied to a user's arm.
Figure 10:
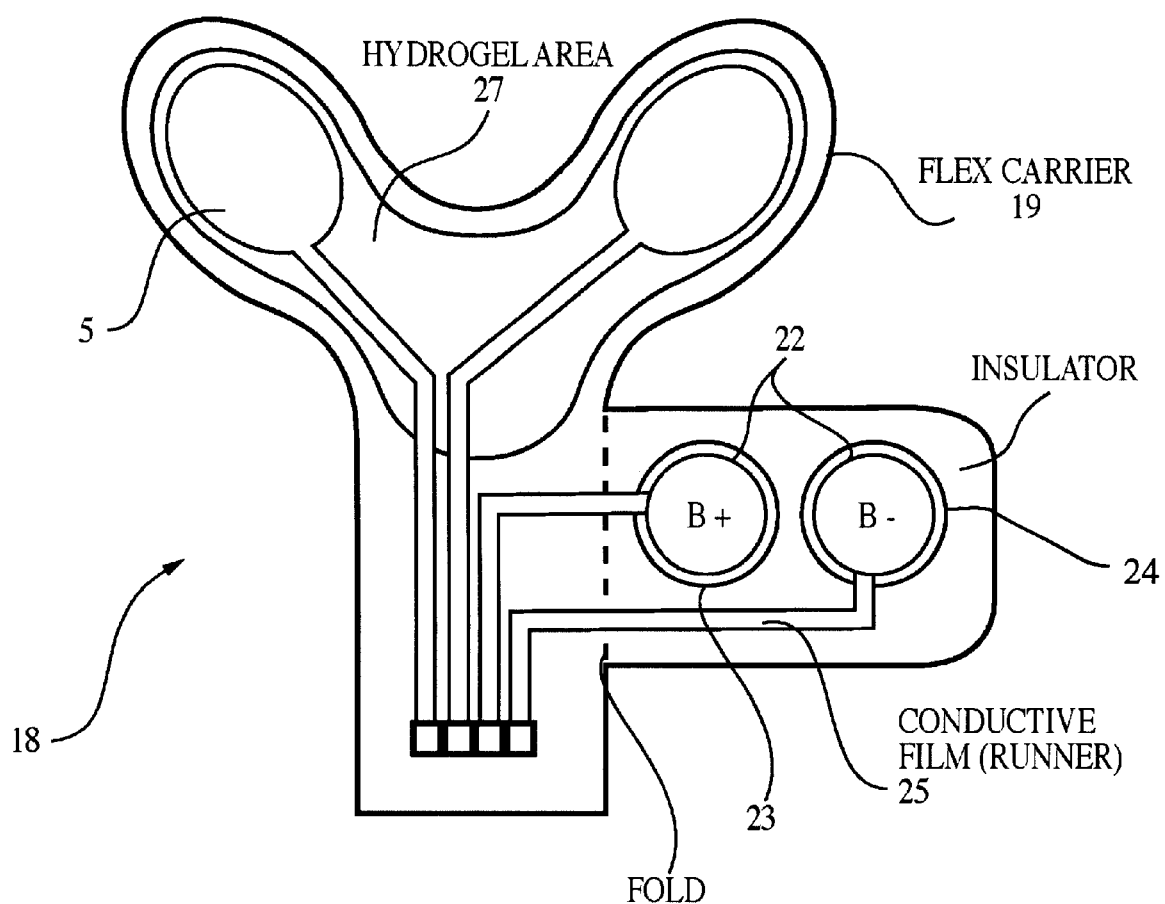
FIG. 10 shows an overhead view of the electrode-battery assembly 18.
Figure 18:
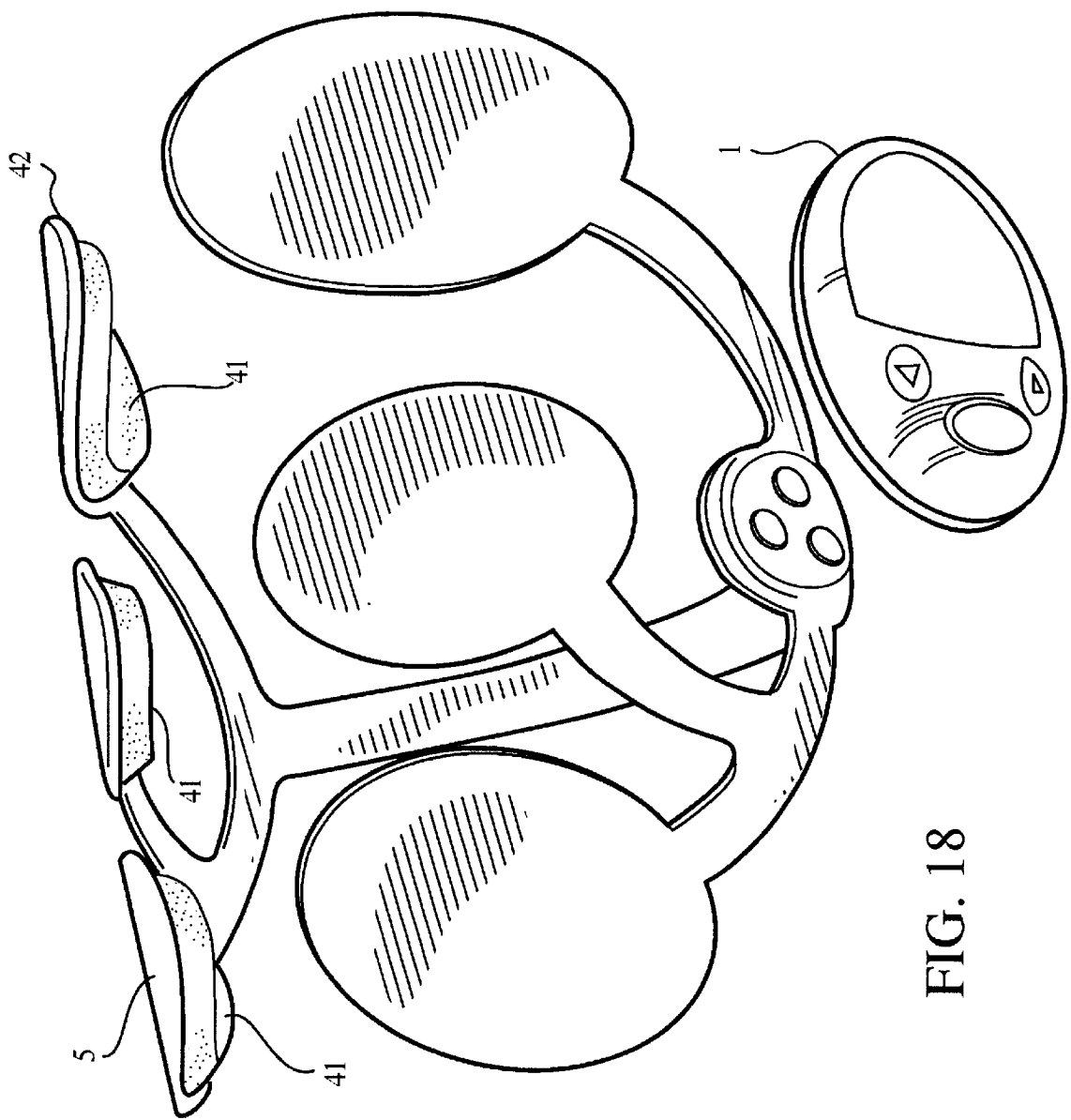
FIG. 18 shows an alternative exploded perspective view of the housing 2 and the electrodes 5 for use in conjunction with the cast 36 of FIG. 14.

A plurality of electrodes 5, as seen in FIG. 3 each having an internal side 42 and an external side 41 (see FIG. 18), are attached to the housing 2. The electrodes 5 come in various shapes and sizes and can be disposable or non-disposable. The various types of electrode configurations can be seen in FIGS. 4a–4l. The various electrode configurations can be placed in a number of different locations on the user's body including but not limited to: the neck; wrist; shoulder; the elbow or forearm; the hand or a finger; scapula; abdomen; lower back; knee; hip; buttocks; thigh; or ankle. The electrodes 5 are affixed directly to a pain site or other area requiring electro or muscular-stimulation anywhere on the user's body as illustrated in FIG. 5 and FIG. 6. Attached to the electrodes 5 is a flexible non-conductive carrier 19, as seen in FIG. 10, which carries current to a pain site requiring electrical neuro or muscular-stimulation via the electrodes 5. The electrodes 5 are either fixed or able to swivel at each connection point to allow for optimal electrode placement at each pain site.

The electronics module 20 is located within the housing 2 and is comprised of an electrical circuit 21 which provides a biphasic or monophasic sequence of pulses to the electrodes 5. It has several pre-programmable waveforms that are available for a variety of specific clinical needs. The electronics module 20 within the housing 2 is detachable and disposable and able to be snapped into and out of each miniature wireless transcutaneous electrical neuro or muscular-stimulation unit 1.

Figure 7:
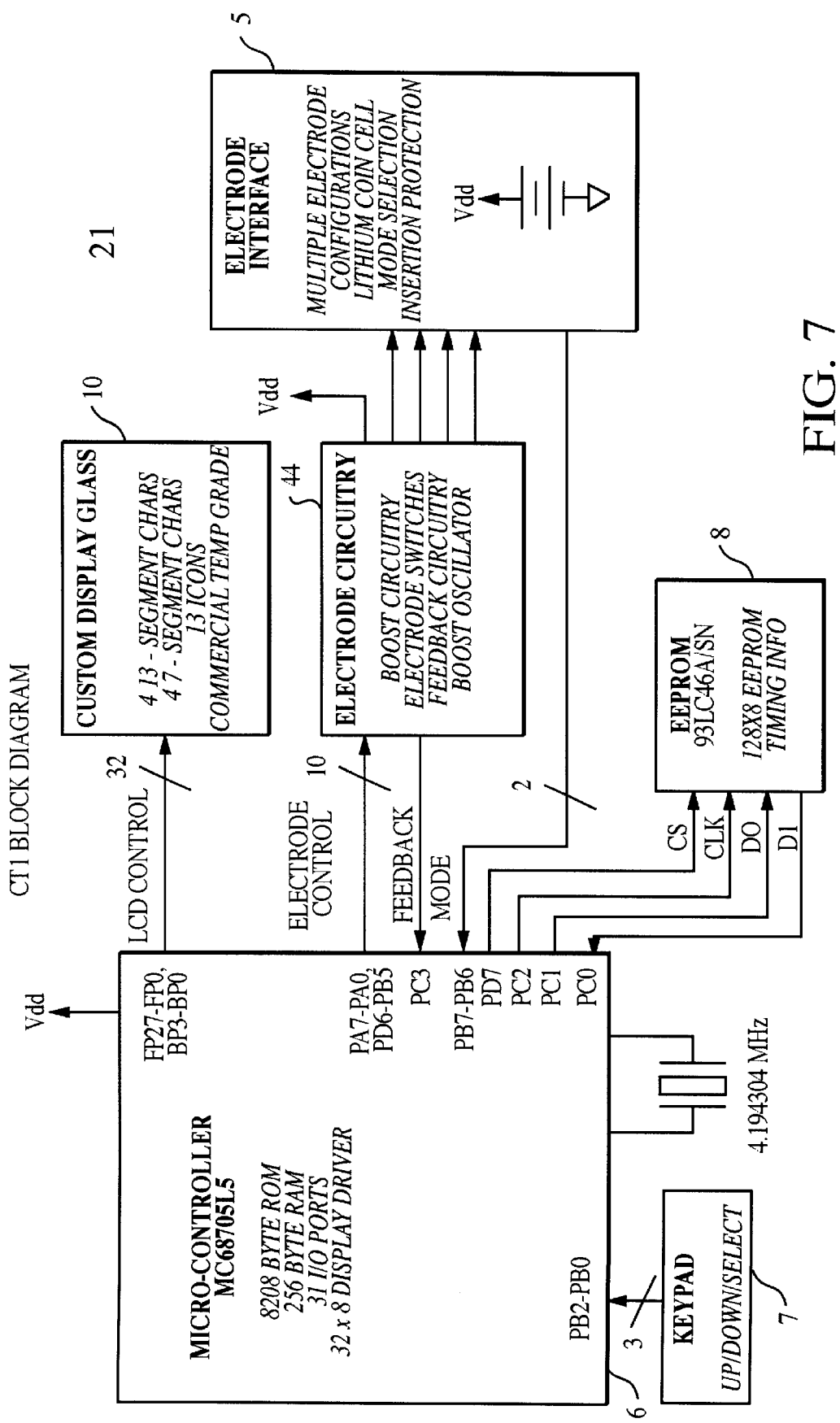
FIG. 7 shows a block diagram of the electrical circuit used in the miniature wireless transcutaneous electrical neuro or muscular-stimulation unit 1.
Figure 8:
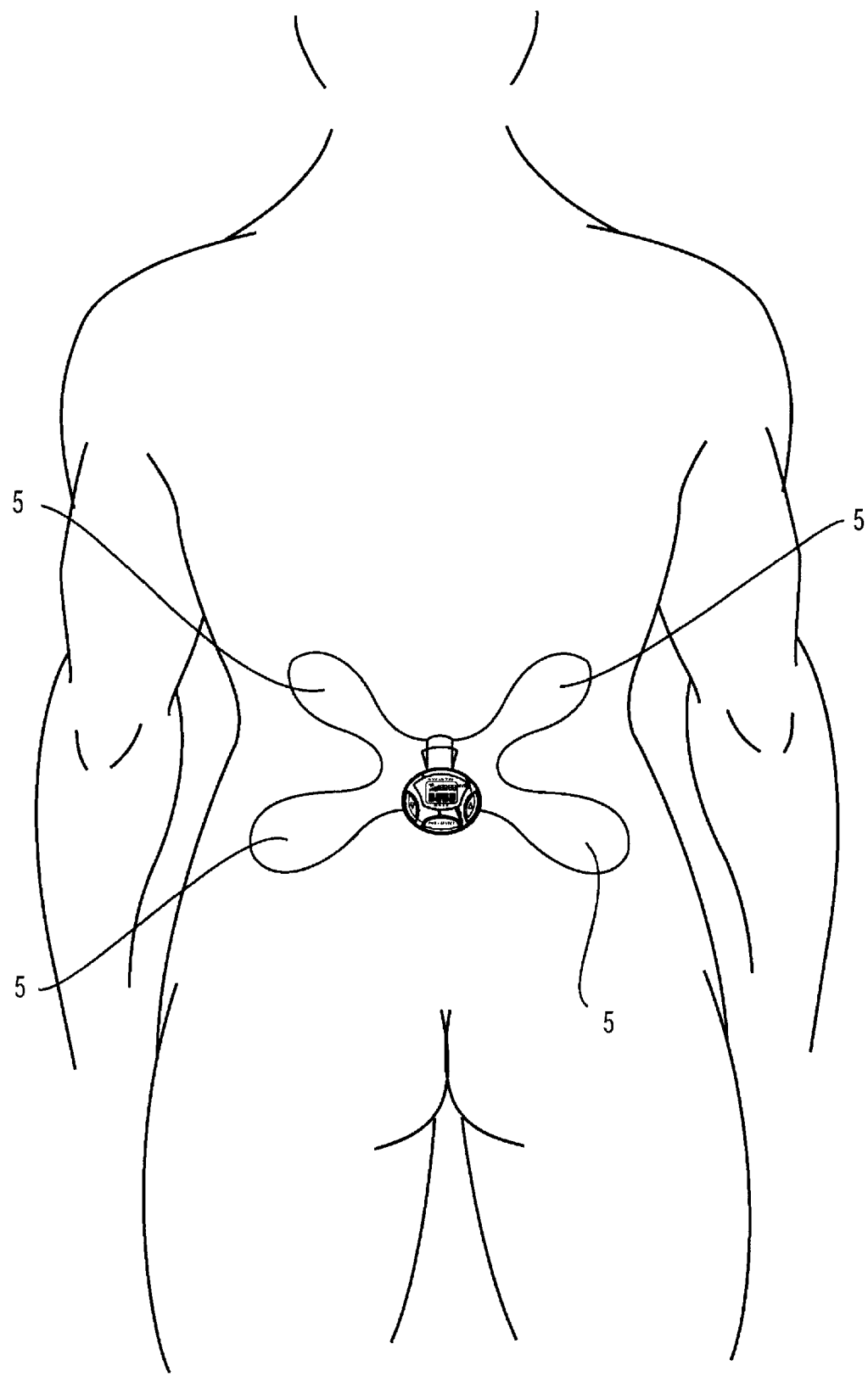
FIG. 8 shows an overhead view of the electrodes 5 attached to a miniature wireless transcutaneous electrical neuro or muscular-stimulation unit 1, placed on a user's lower back.

Contained within the electronics module 20 is an electrical circuit shown in the block diagram format of FIG. 7. The miniature wireless transcutaneous electrical neuro or muscular-stimulation unit 1 of the present invention utilizes a microprocessor 6, the MOT68HL0515, know as "Cheap Chip." This is a derivative of the 6502-05 microprocessor.

The MOT68HL0515 comes with a 16×8 LCD driver, 128 Byte RAM, 10 I/O ports, a D/A port and an on board real time clock circuit to maintain time even through stop modes. Its primary features are its large 6.5 Kbytes ROM space and display driver capabilities. Assembly language is utilized to program the MOT68HL0515. The microprocessor 6 interfaces with a keypad 7; the EEPROM 8 which its large 6.5 Kbytes ROM space and display driver capabilities. One or more batteries 22 supply power to the electronics module 20 wherein the batteries 22 can be placed in a battery housing of the interface plate which connects to the bottom of the electronics module 20 or can be integrated with the electrodes 5 in one assembly. The batteries 22 may be either replaceable or rechargeable. Lithium or alkaline batteries may be used for the disposable applications. NiCd and NiMH may be used for the rechargeable applications.

The voltage drop on a lithium battery is very small across the life of the battery. A full charged cell is approximately 3.3 volts and can dip as low as 2.7 volts. This gives an adequate voltage range for operation of the electronic circuit 21. To accomplish the same result with alkaline cells, at least 2 or 3 batteries must be used to insure that the proper voltage level is kept. The voltage range on the life of a double "A" alkaline battery is 1.6–0.9 volts. Using 3 batteries yields a range of 4.8–2.7 volts.

A series of one or more protrusions within the housing 2 provide a means to restrict the waveforms available to those appropriate for each particular electrode 5 and treatment. These protrusions interface with the electronics module 20 to determine the waveforms which may be used.

A user may select and control specific waveforms and the intensities of a number of various modes at the site of an electrode 5, as well as the orientation and quantity of the electrodes 5.

Once the specific waveform and intensity are selected, the user can identify the waveform chosen, its intensity, and its duration by use of a series of buttons controlling an LCD display 10 as shown in FIG. 1. The LCD display 10 stores and displays time of usage for each mode. These buttons can also control the intensity of the biphasic or monophasic sequence of pulses.

The LCD display 10 has a 4-character starburst display for displaying mode 13, an elapsed time/mode digital readout 14, an intensity bar 15, an enunciator 12 and may be eluminated by an electro-luminescent backlight. This light remains on for five seconds after each button is depressed. The LCD display 10 also consists of icons, digits, and Starburst characters. One of the icons, the power icon 16, is used to show when the unit is on. Another icon, the cycling icon 17, is used to show when the cycling mode is active.

The digits displayed by the digital readout 14 are used to display the elapsed time of any of the selected modes. The units are in hours and minutes with the maximum being 99 hours and 59 minutes. If the miniature wireless transcutaneous electrical neuro or muscular-stimulation unit 1 is turned off, the elapsed time for each individual mode is stored inside of the EEPROM 8 and can be retrieved later upon powering up the miniature wireless transcutaneous electrical neuro or muscular-stimulation unit 1. The EEPROM 8 size is a 4K bit part. It is used to store elapsed time information from the individual modes as well as the last mode that the device was set at. Scrolling to "RSET" and then depressing the select button will reset the mode times.

The Starburst characters display each mode, and are represented by the following different mode names:

CON2—Conventional High
CON1—Conventional Low
MOD2—Modulation High
MOD1—Modulation Low
ACU2—Acupuncture-like, high
ACU1—Acupuncture-like, low
MICR—Microcurrent
BRST—Burst
OFF—Turn unit off
CYCL—Enter Cycling Mode
RSET—Reset all elapsed times to zero.

Another miniature wireless transcutaneous electrical neuro or muscular-stimulation unit 1 configuration, the CT3 model, provides, in addition to the modes listed above, alternate muscle stimulation modes, primarily for muscle rehabilitation. This configuration is also a non-remote, locally-controlled unit. Other than the difference in modes, the characteristics of each configuration is similar.

The number of modes to choose from in this alternate configuration consists of but is not limited to a three different muscle stimulation modes, a conventional mode, a modulation modes and three cycling modes.

The Starburst characters display each mode for the CT3 model, and are represented by the following different mode names:

MS05—First Muscle Stimulation Mode
MS10—Second Muscle Stimulation Mode
MS50—Third Muscle Stimulation Mode
CON2—Conventional High
MOD2—Modulation High
CY05—First Cycling Mode
CY10—Second Cycling Mode
CY50—Third Cycling Mode
OFF—Turn unit off
RSET—Reset all elapsed times to zero As with the first configuration (CT-1), whenever the devices are automatically changing intensities, there will always be a 2 second ramp up and/or a 2 second ramp down.

Figure 9A:
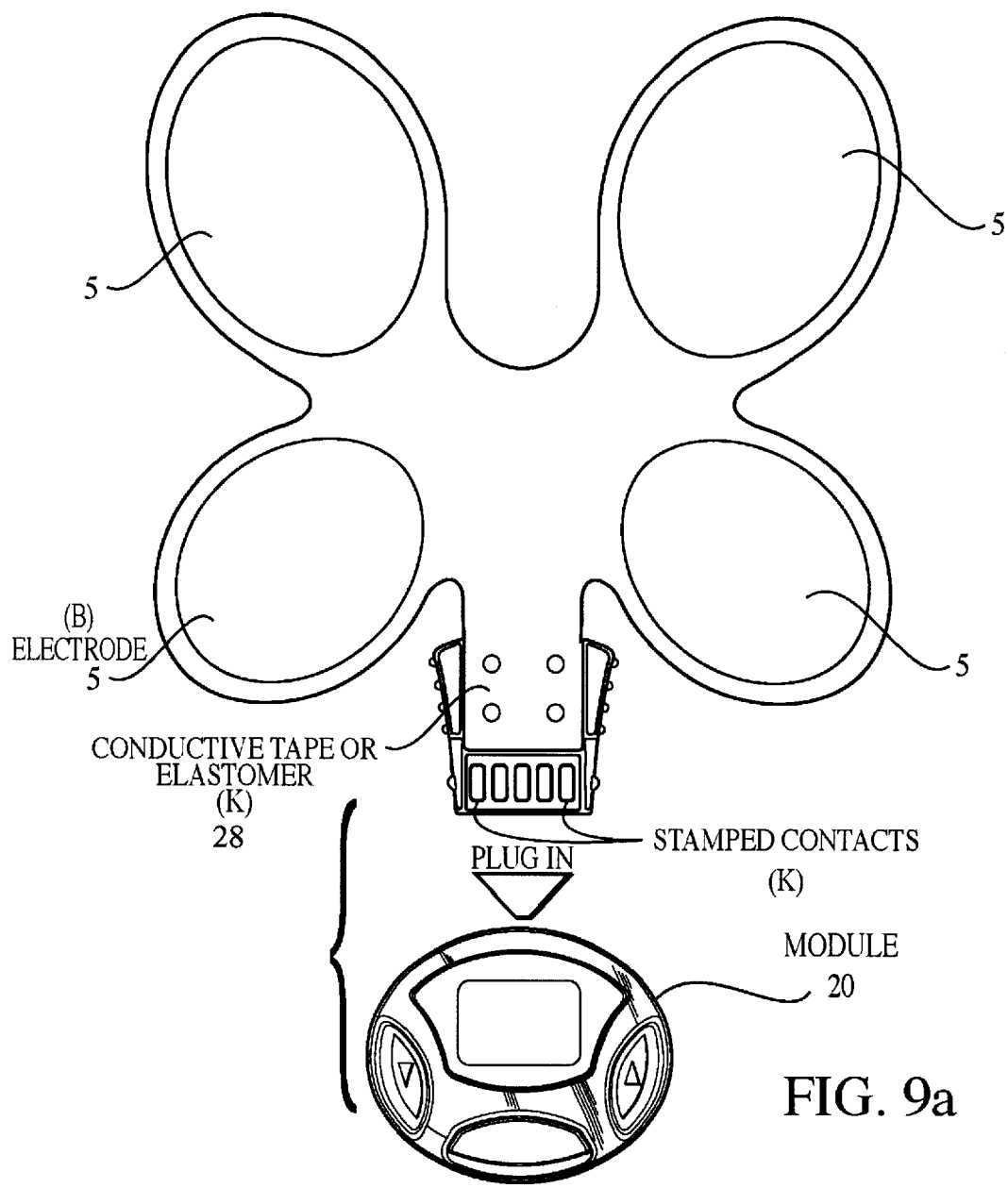
FIGS. 9a–b show overhead and side views of an electrode 5 connected to the electronics module 20.
Figure 9B:
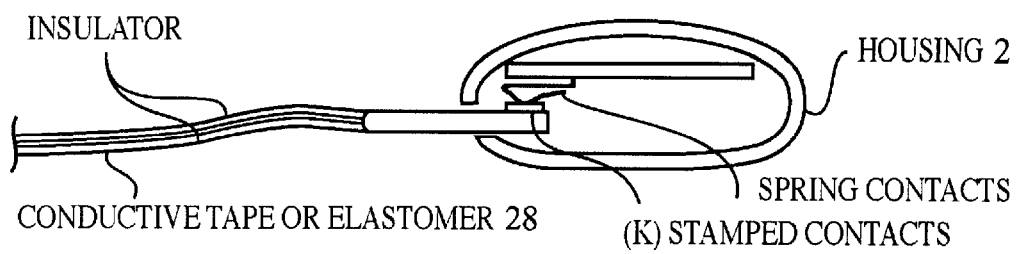
Figure 11:
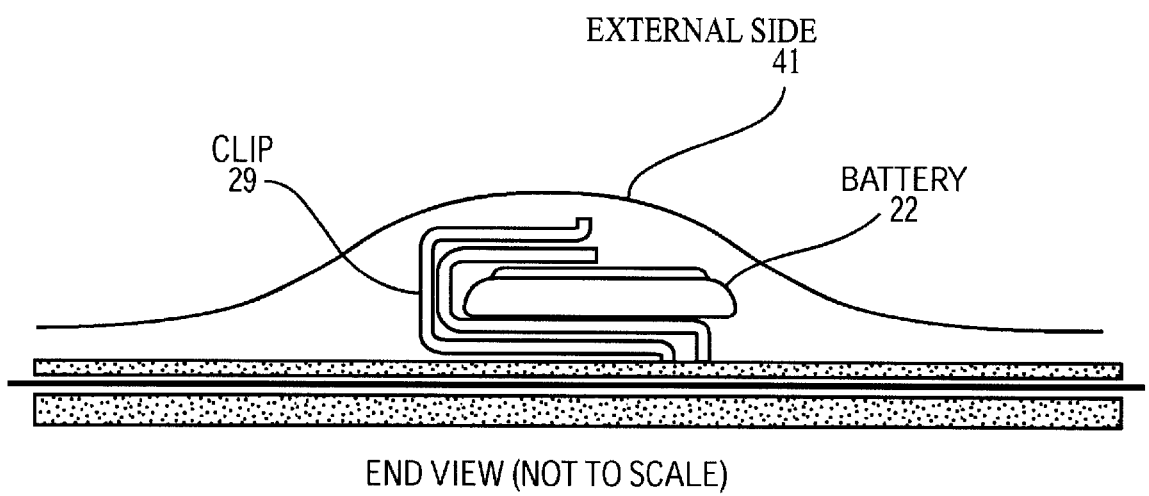
FIG. 11 shows an end view of the electrode-battery assembly 18 of FIG. 10.
Figure 12:
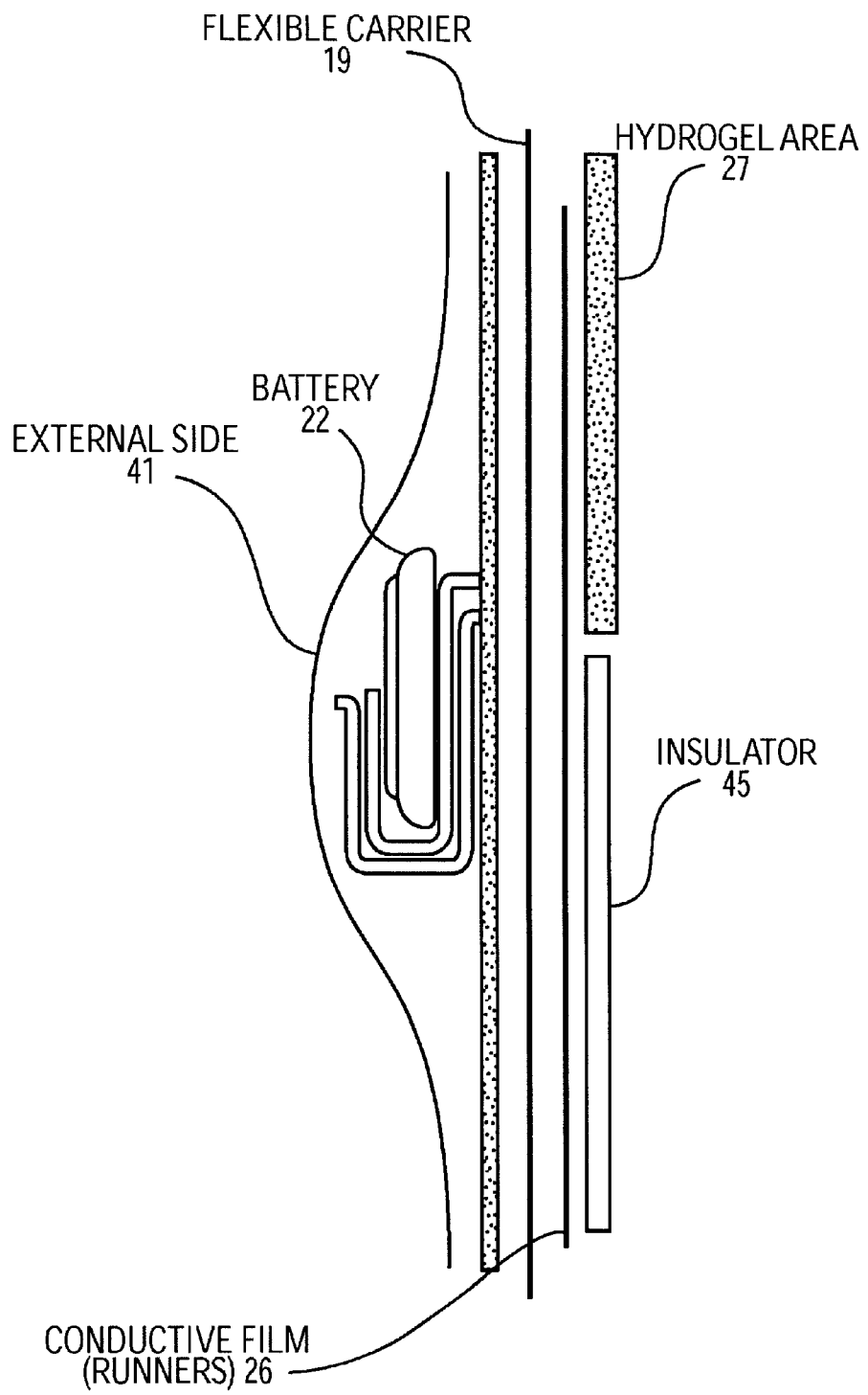
FIG. 12 shows a side view of the electrode-battery assembly 18 of FIG. 10.
Figure 17:
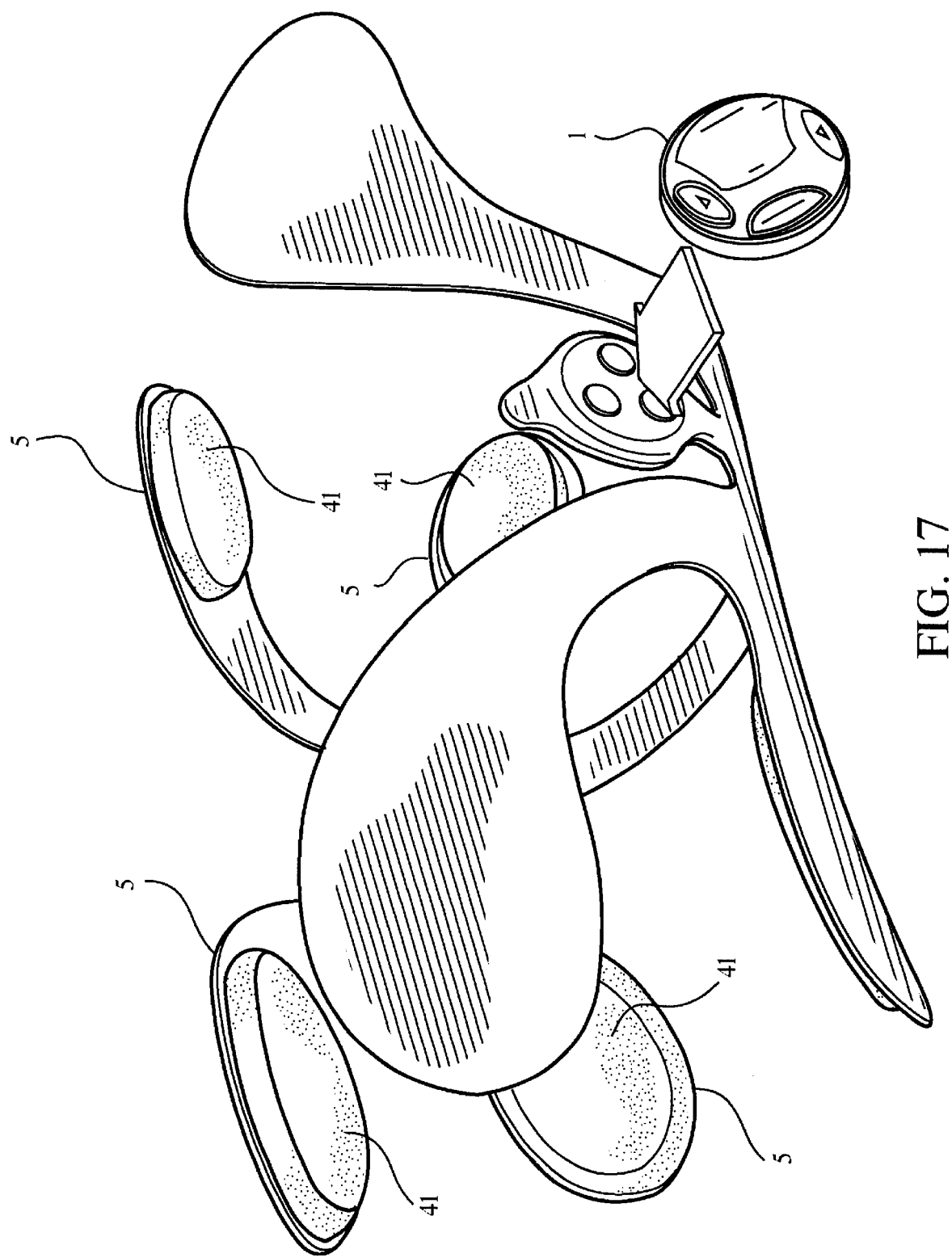
FIG. 17 shows an exploded perspective view of the housing 2 and the electrodes 5 for use in conjunction with the cast 36 of FIG. 14.

A disposable electrode-battery assembly 18, as seen in FIGS. 10, 11 and 12, resides within the housing 2 of the present invention. FIG. 10 shows the assembly 18 comprised of a plurality of electrodes 5 each having an internal and external side and a plurality of batteries 22 each having a positive pole 23 and a negative pole 24. Current carrying runners 25 comprise a conductive film 26. Two of these runners 25 make direct contact to the positive 23 and negative 24 poles of the battery 22, while the third makes contact with conductive hydrogel 27 which carries the stimulating current to the patient via each electrode 5. Contact to the battery poles is secured either by a conductive adhesive 28 as seen in FIG. 9 or a mechanical clip 29 as seen in FIG. 11. in order to apply the required pressure. The conductive film 26 may be a silver alloy film or other flexible low impedance material. The external side 41 of the electrode 5 is covered by soft cosmetically appealing molded foam or elastomer as seen in FIG. 17. Once the battery 22 is depleted, the entire electrode-battery assembly 18 can be disposed of or replaced. The unique advantage provided by the electrode/battery assembly 18 is its ability to combine both the electrodes 5 and batteries 22 in one separate housing thereby supporting different battery technologies. Therefore, the housing 2 can be produced in large quantities regardless of the type of battery configuration utilized as long as the housing 2 is designed with the requirement that 3 volts are to be provided to it.

Figure 13A:
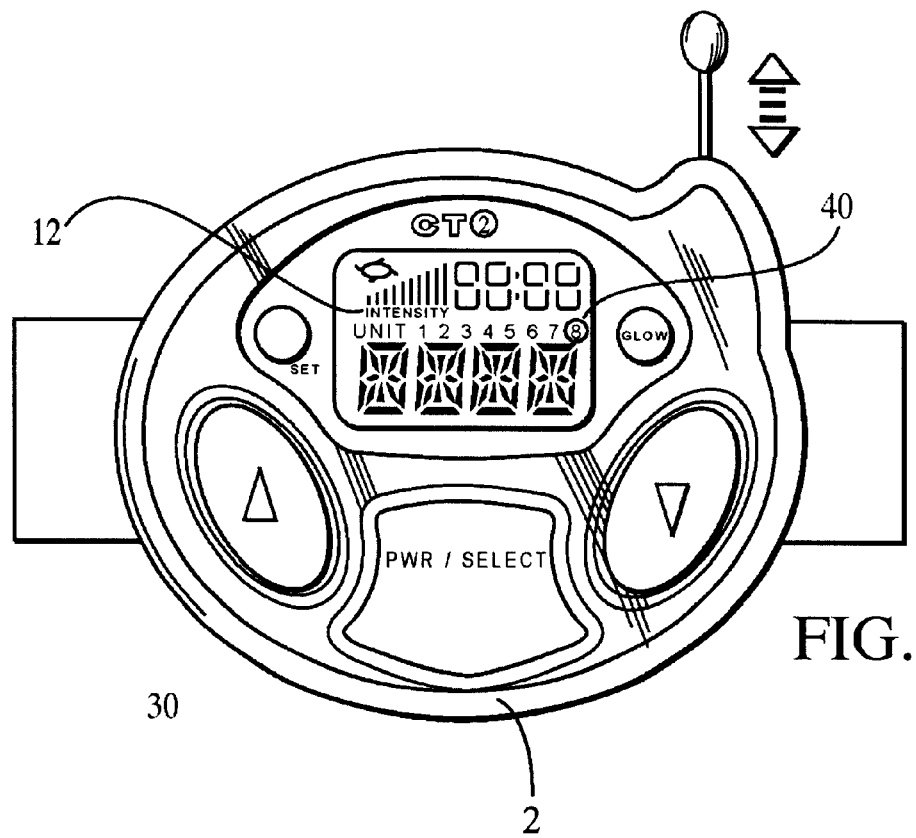
FIG. 13 shows overhead and perspective views of a remote controller 30 to be worn on a user's wrist.
Figure 13:
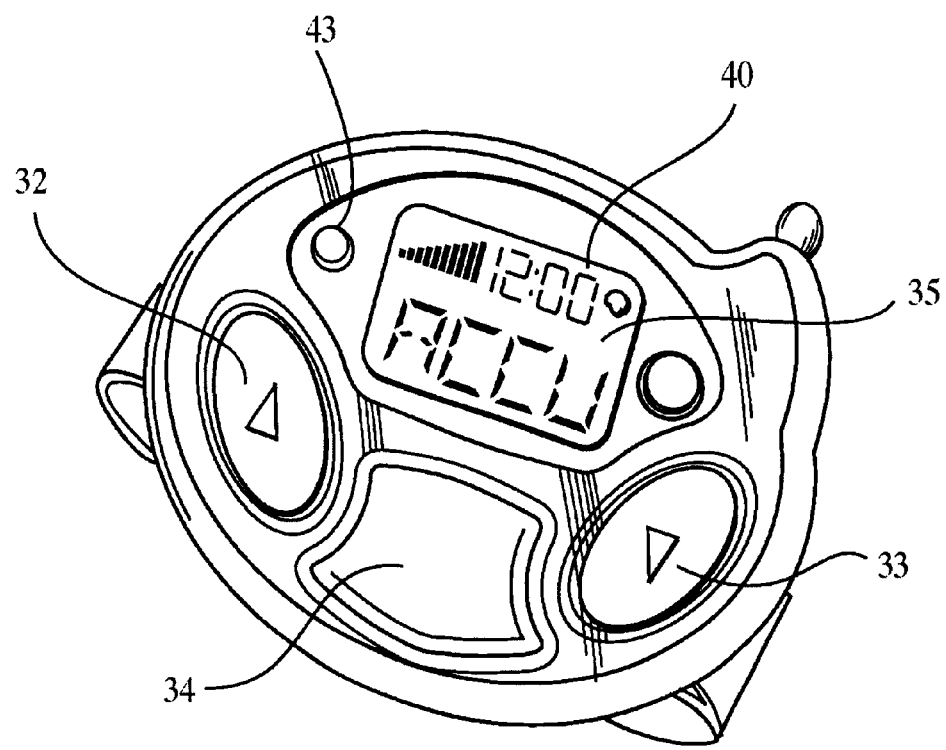
Figure 14:
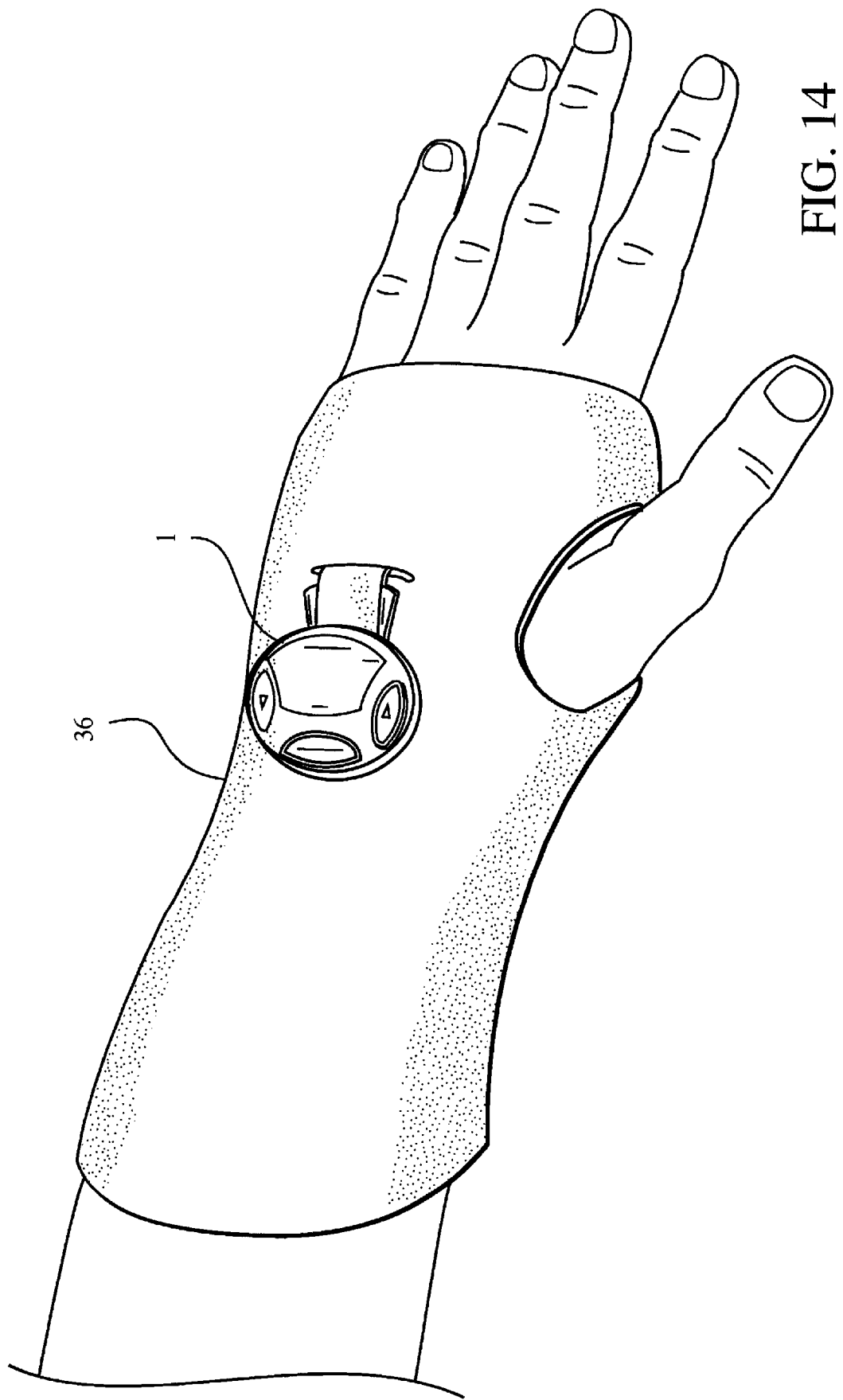
FIG. 14 shows a perspective view of a standard cast 36 used with the present invention.
Figure 15:
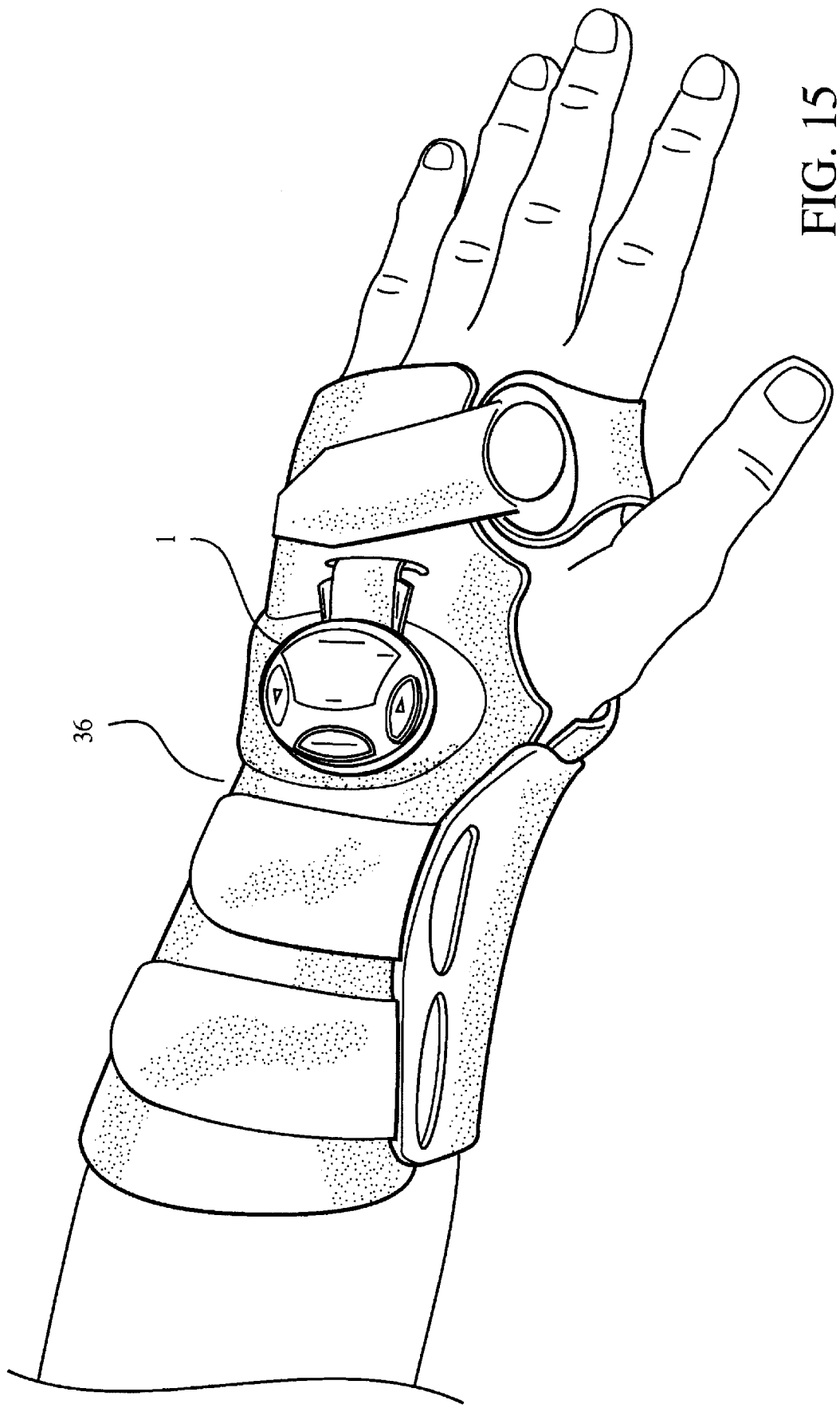
FIG. 15 shows a perspective view of the cast 36 of FIG. 14 on a user's wrist and forearm.

The miniature wireless transcutaneous electrical neuro or muscular-stimulation unit 1 of the present invention is capable of featuring a controller 30 or transmitting device which includes a time function, a carrier signal capable of sending signals in a digital format, a display enunciator 40 which provides means of identifying individual receivers, a synchronizing pulse, and means for individually setting the waveform mode, intensity and time duration of multiple remote electrode assemblies 18. The controller 30, as seen in FIG. 13, can be worn on a comfortable site on said user's body, such as the wrist. The controller 30 sends a radio frequency, low-powered transmission signal of less than 1 Watt of effective radiated power, via a transmitting conductive plate, transducer, or antenna placed on the controller to the unit 1, which has a receiving conductive plate, transducer, or antenna, respectively to receive said transmission signal. This is done by the use of a capacitive coupling having a plurality of conductive plates placed near the surface of the user's skin wherein one of the metallic plates resides in the controller 30 and the other conductive plate or transducer resides in the unit 1, using the user's body as a conductive medium to transmit the transmission signals.

An alternate form uses over-the-air RF transmission by having a plurality of antennas placed inside of the controller 30 and the other antenna resides in the unit 1.

An alternate means for individually setting the waveform mode, intensity and time duration of multiple remote electrode assemblies 18, is via a tether which can be snapped into the electronics module 20 at one end of the tether and a docking station at the other end of the tether. Once the mode and intensities have been set by the patient, the tether is detached from the electronics module 20 and docking station. The electronics module 20 is then placed directly into the docking station maintaining the mode and intensities that were set via the tether. The tether is then detached and stored in a remote location or wound on a recoil spring in the electronics module 20, docking station, or some other assembly.

The docking station provides the patient flexibility in selecting the appropriate battery configuration given varying factors including cost, size and time of use. Many docking station configurations exist, however each contains battery contacts for battery 22 connection and electrode contacts for electrode 5 connections.

One docking station configuration comprises button cell or cylindrical cell batteries; a housing with mating features to the electronics module 20, and which houses the batteries; a circuit board with battery contacts for connection to the electronics module 20 and the batteries; and a voltage regulator and female jacks for accepting lead wires from the electrodes 5. In an alternate embodiment of the docking station described above, mechanical clamping means are used to attach electrode conductive material directly to the circuit board, as opposed to lead wires. In yet another embodiment of the docking station, the batteries are placed directly over the electrodes 5 as an assembly of the electrodes 5. This can be accomplished either with or without the use of lead wires.

Yet another docking station configuration comprises a lithium polymer battery assembled as a flexible layer uniquely integrated as part of the electrode/battery assembly 18. Replacing the traditional batteries 22 of the traditional electrode/battery assembly 18 described above is a lithium polymer battery assembled as a flexible lithium-ion polymer battery layer, and an insulation layer. The advantage of this assembly 18 is its low-profile design that makes the batteries virtually invisible to the user. The assembly 18 is lightweight, flexible and has superior conformability and rechargeability features. The disposable electrodes 5 can be removed and replaced by pealing the durable lithium polymer layer away from the insulation layer.

Finally, any of the above docking station configurations can be used as an integral assembly to a standard splint, bandage, manufactured brace, or cast 36.

The signals can be transmitted from the controller 30 to the unit 1 either through the user's body at between 40–500 kHz, or via over-the-air RF transmission at frequencies of between 40 kHz–915 MHz. The transmission signals are synchronized to the unit's monophasic or biphasic sequence of pulses to avoid interference. A means of synchronizing the electrodes 5 is provided such that the polarities of the electrodes 5 are 180 degrees out of phase thereby causing electrons to be exchanged between the electrodes 5. The controller 30 has a display means 31 indicating time of usage for each mode. The means for allowing the user to select and control the modes is through a series of input keys 32–34 controlling an LCD digital readout display 35 on the controller 30. The unit 1 acts as a remote module with display means and, by setting its software address, allows itself to be identified by the remote controller 30, which sends transmissions signals to an identifiable remote module.

Figure 16:
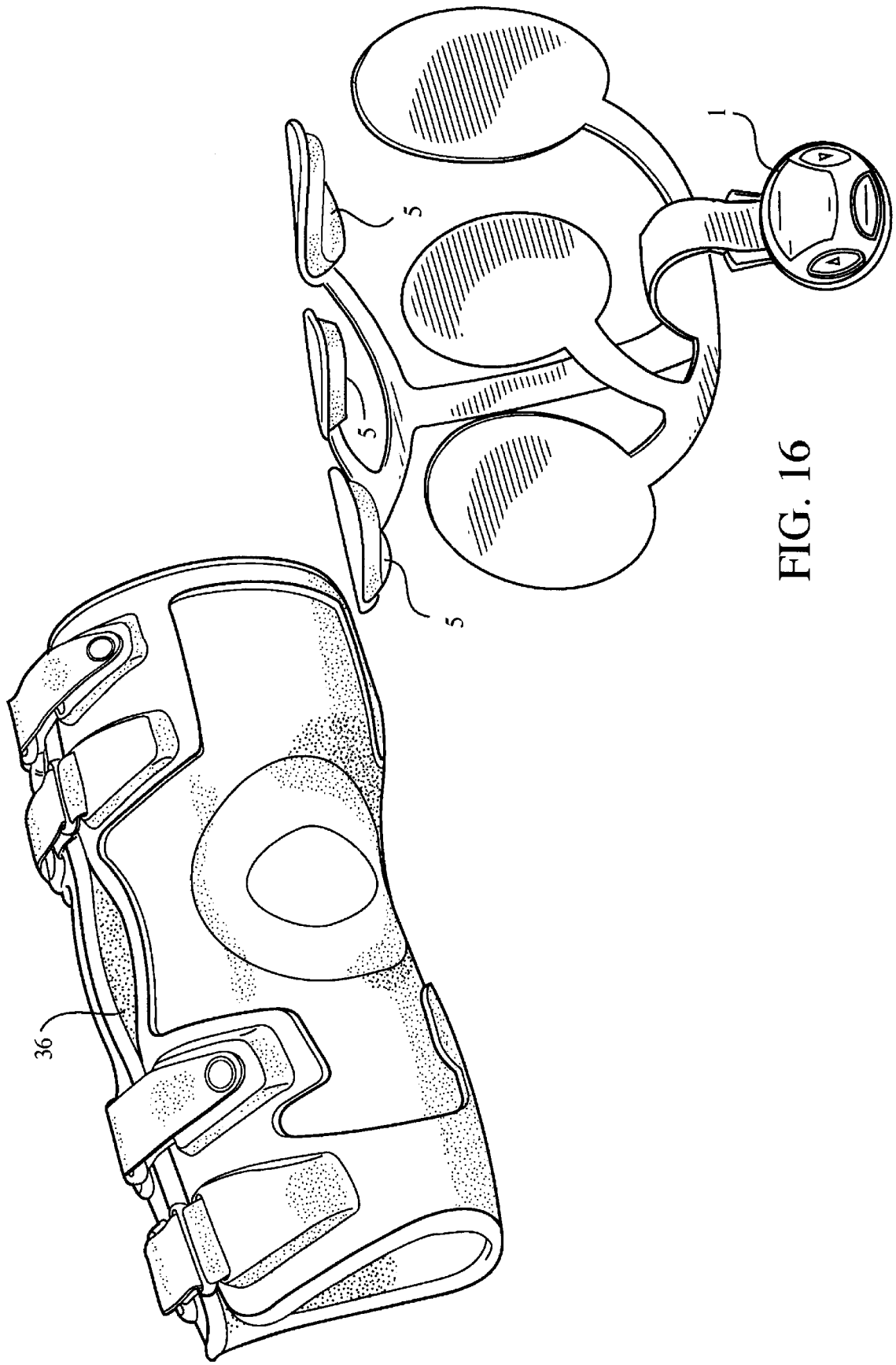
FIG. 16 shows an exploded perspective view of the housing 2, electrodes 5 cast 36.
Figure 19:
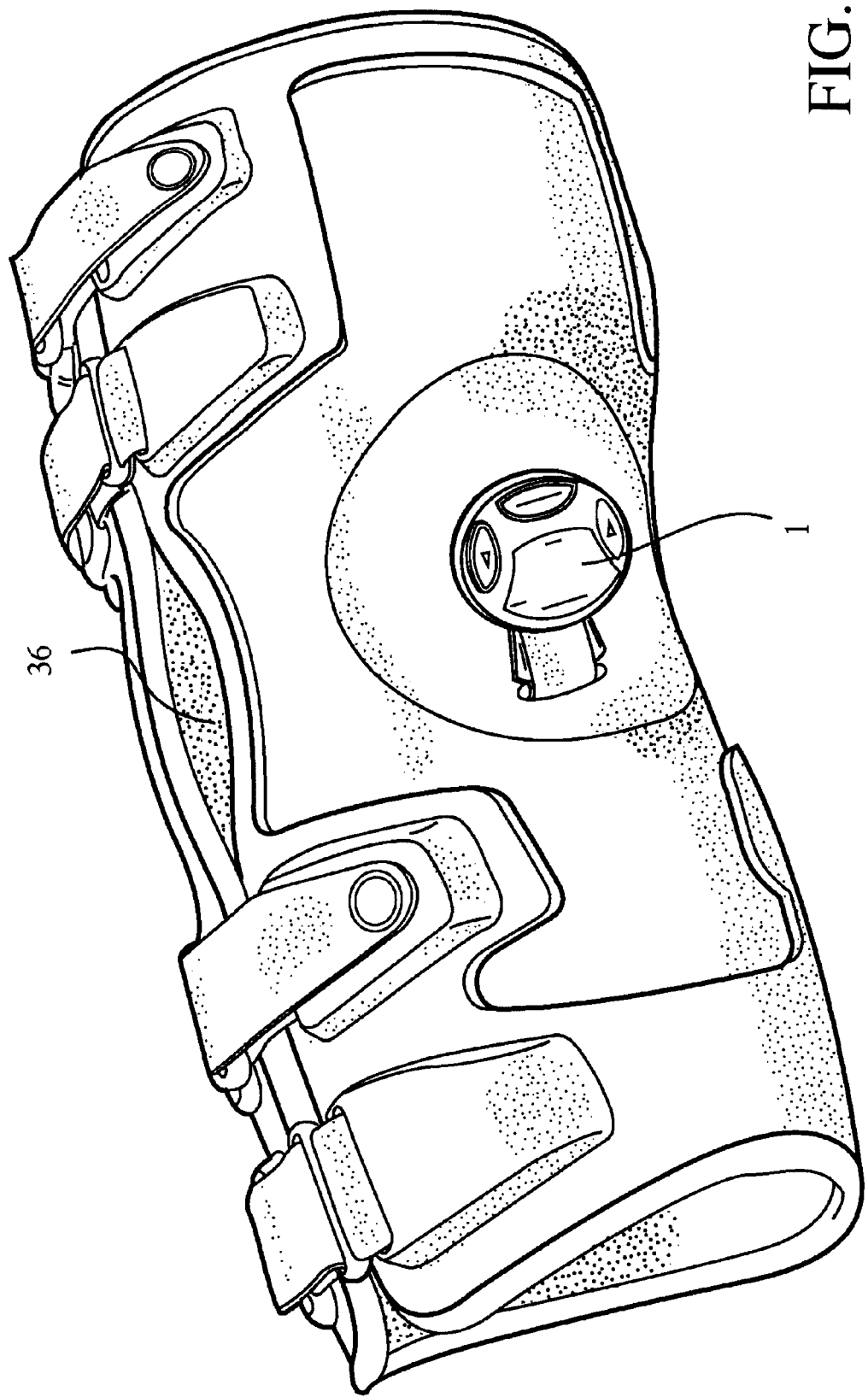
FIG. 19 shows a perspective view of the cast 36 with the housing 2 and electrodes 5 (not shown) embedded within the cast 36.
Figure 20:
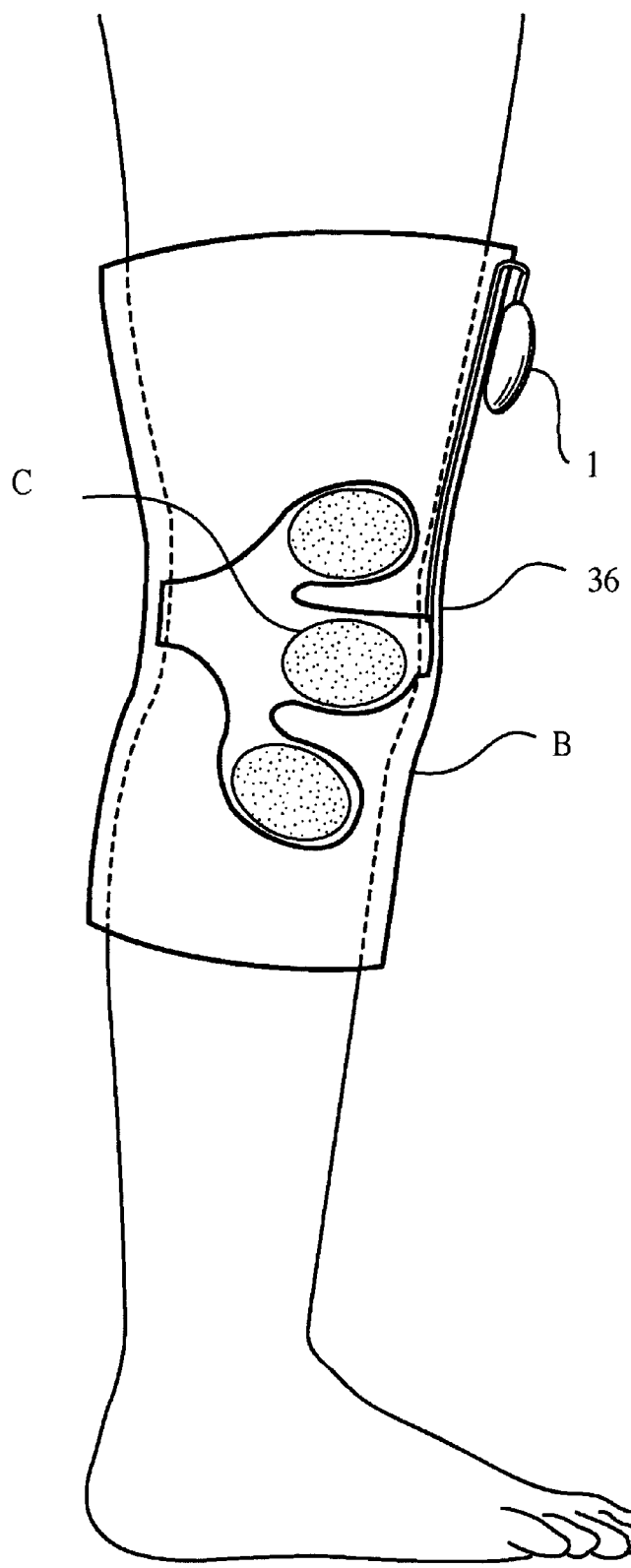
FIG. 20 shows a side view of a cast 36 with embedded housing 2 and electrodes 5 used on a user's knee.
Figure 21:
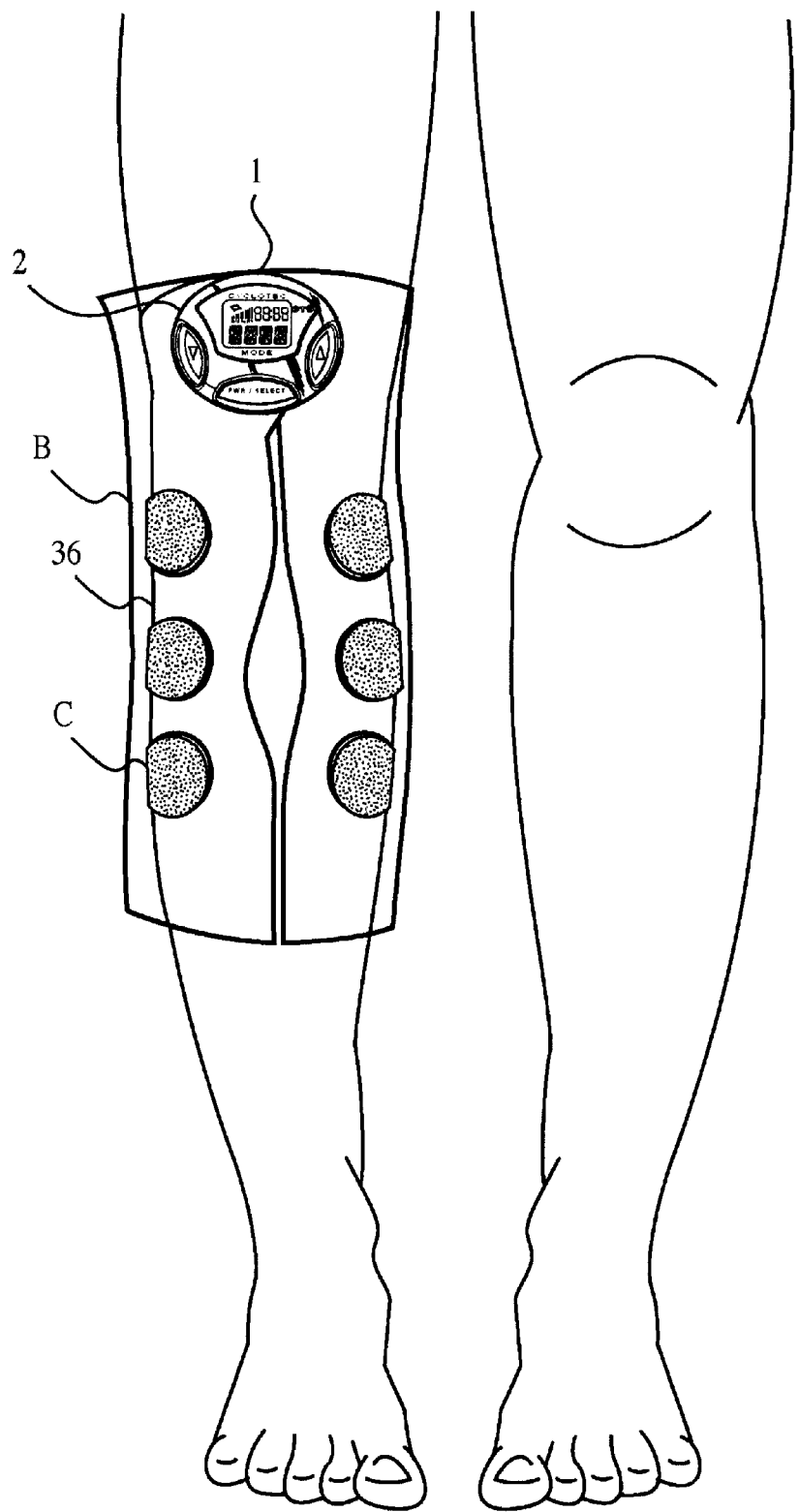
FIG. 21 shows a front view of a cast 36 with embedded housing 2 and electrodes 5 used on a user's knee.

The unit 1 is also capable of being attached, implanted or molded into a standard splint, bandage, manufactured brace, or cast 36 as seen in FIGS. 14–19. The electrodes 5 are arranged in a grid-like manner to allow for programming of a specific firing order which can provide for greater therapeutic effect to the pain site. A plurality of post-surgical incisional electrodes 5 are embedded in the splint, bandage, brace, or cast, as shown in FIGS. 16 and 19. Multiple layers of non-visible wires or flex-circuit material provide for connection between the electrodes 5 and the unit 1.

In an alternate embodiment, the unit 1 can be incorporated into a "Band-Aid-like" device, similar to that of a conventional Band-Aid. It includes the miniaturized electronics module 20 having conventional-low or modulation-low and microcurrent stimulation modes identical to those in the preferred embodiment. A gauze pad impregnated with an antibacterial agent is placed adjacent to and generally underneath the electronics module 20. A single LED or other similar indicating device indicates that the unit 1 is powered up. One or more batteries 22 supply power to the electronics module 20. The stimulation modes can be adjusted between the conventional or modulation low mode, used primarily in daytime and the microcurrent mode, used primarily at nighttime. Intensity levels of each mode can also be adjusted via an adjusting means.

The "Band-Aid-like" device contains adjacent adhesive sections which are comprised of the conductive electrodes 5. The device can be activated by simply applying it to the patient's skin without the need for any switching means, and is packaged and sterile wrapped in a similar fashion to that of conventional Band-Aids.

In order for a patient to use the miniature wireless transcutaneous electrical neuro or muscular-stimulation unit 1, the patient must first activate the unit 1 by holding down the SELECT button 37 for two seconds. "DISPLAY" appears and "MODE" blinks. The patient then selects either the UP arrow 38 or the DOWN arrow 39, which will scroll through the available modes. When the desired mode is blinking, the patient depresses the SELECT button 37. The "MODE" display stops blinking, and the "INTENSITY" icon 12 begins blinking. The user can adjust the intensity by pressing the UP 38 and DOWN 39 arrows to attain a desired comfort level. The user then presses the SELECT button 37 to accept the intensity shown, and the display ceases to blink.

To activate the CYCLE mode, the user presets each mode to be included by using the above method. Modes preset with an intensity level of zero are skipped in cycling. When all modes and intensities have been selected, the patient depresses the UP 38 and DOWN 39 arrows until the word "cycle" appears in the mode selection window. The user then presses the SELECT button 37 to begin cycling. When modes change, the intensity will ramp over a period of 5 seconds, from a value of zero, to the value of the previously set intensity.

If the user wishes to adjust the intensity during operation, this is done by pressing the SELECT button 37 twice. After the first depression, "MODE" will start blinking. After the second depression, "INTENSITY" will start blinking. While "INTENSITY" is blinking, the UP 38 and DOWN 39 arrows can be depressed to adjust the intensity. During the cycling mode, each mode will ramp up for over 5 seconds from a value of zero to the value of the previously set intensity. During the ramp-up, and for 10 seconds thereafter, the user may re-adjust the intensity.

If the remote controller 30 is to be used, it is necessary to first select a particular unit on the user's body. Upon powering up the controller 30 by using the power button 43, the message "UNIT #" appears on the display enunciator 40 and a digit flashes below to the enunciator 12. The user can scroll between 1 and 8, each representing a different unit, by using the UP key 33 and the DOWN key 34. The user can accept a unit number by depressing the SELECT key 34. This will cause the transmitter to repeatedly send out a coded address for this particular number. Each unit 1 on the body having an address identical to the one being transmitted will be powered up and identified by the unit number appearing on the controller 30. At this point, the mode selection process described above can be utilized.

Figure 22:
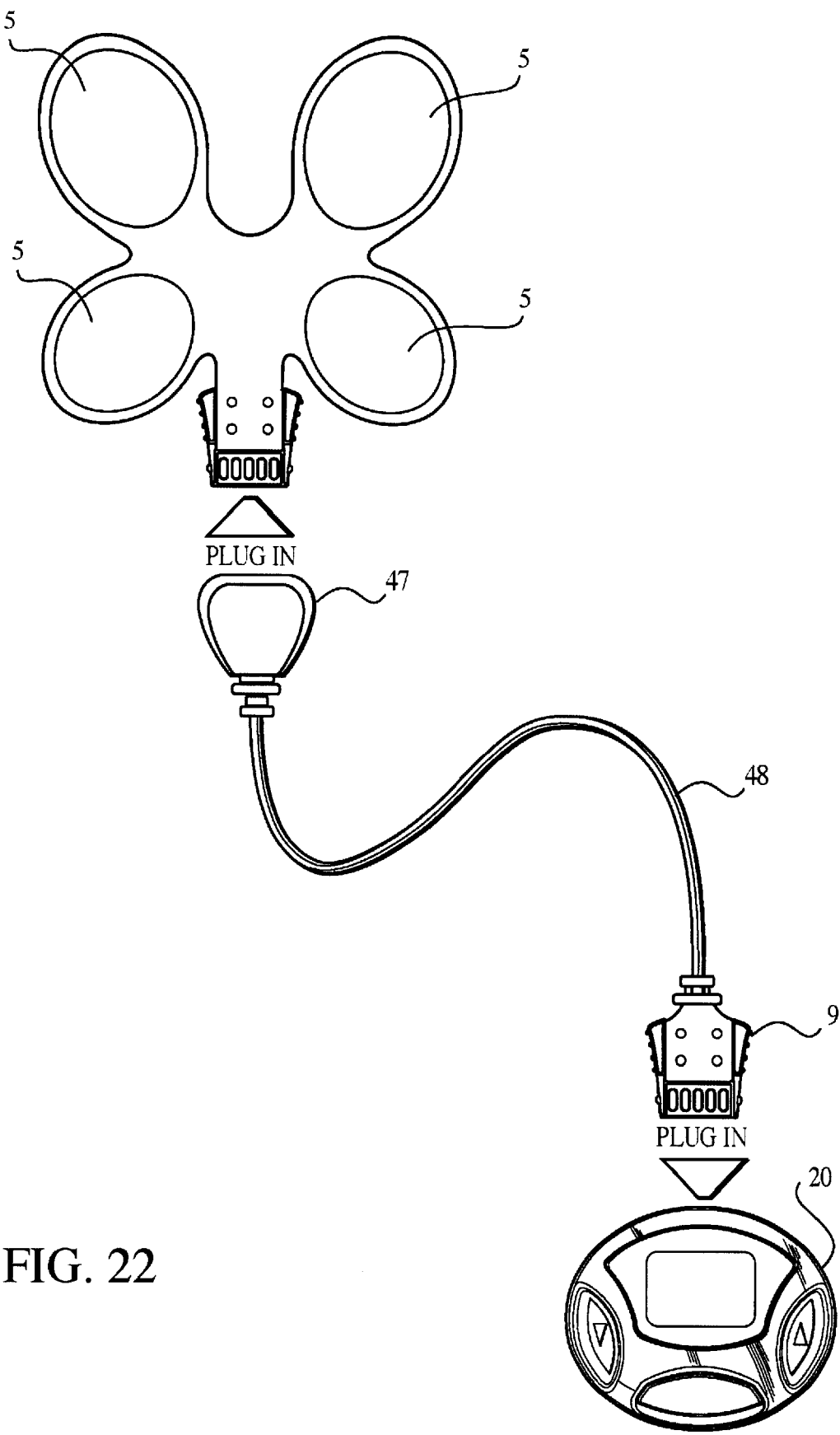
FIG. 22 shows a single-line tether for use in the present invention.
Figure 23:
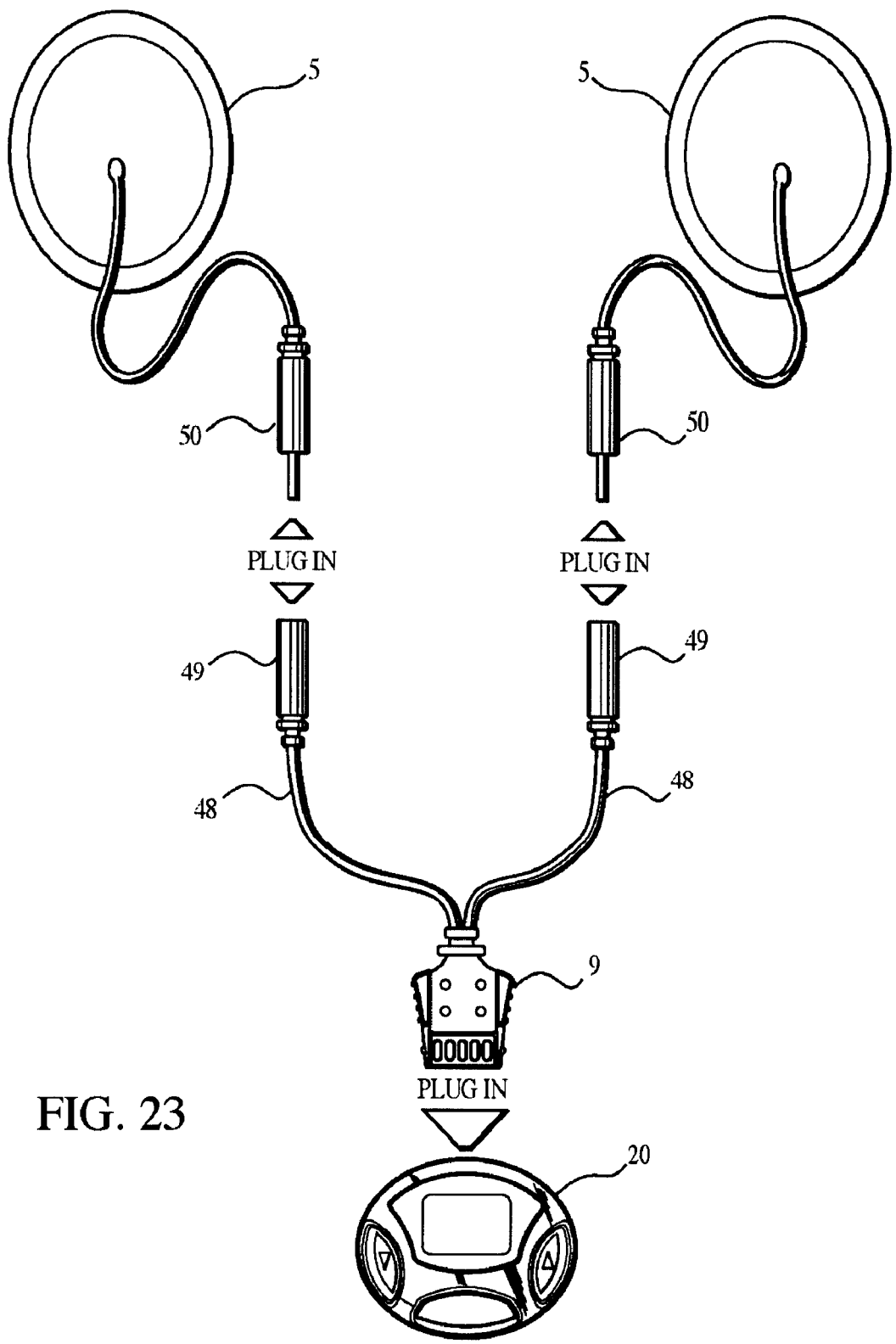
FIG. 23 shows a multi-line tether for use in the present invention.

Looking at FIGS. 22 and 23, the present invention also incorporates a tether line 48 allowing the distance between the control unit 20 and electrodes 5 to be increased, the tether line serving much like a traditional extension cord and permitting connection between the control unit and electrodes without requiring direct connection therebetween. The tether line 48 may consist of a single line, such as is shown in FIG. 22, controlling one set of electrodes 5, or alternatively may consist of multiple lines 48, such as are shown in FIG. 23, each line controlling individual electrodes 5. In the single-line set-up (FIG. 22), the set of electrodes 5 is connected to a tether line 48 using a plug 47. In the multiple-line set-up (FIG. 23), each individual electrode 5 is connected to a tether line 48 using connectors 49 and 50. In both configurations, the control unit 20 is connected to the tether line 48 using a plug 9.

A "Sleep Mode" feature is available which turns the controller 30 and all remote units 1 off, but retains all the latest settings. In this way, the units 1 may be removed, but all of the settings will be recalled the next time they are powered up.

Accordingly, it will be understood that the preferred embodiment of the present invention has been disclosed by way of example and that other modifications and alterations may occur to those skilled in the art without departing from the scope and spirit of the appended claims.

We claim:

1. A miniature transcutaneous electrical neuro or muscular-stimulation unit comprising:

a housing;

a plurality of electrodes attached to said housing;

an electronics module located within said housing and comprising an electrical circuit which provides a biphasic or monophasic sequence of pulses to said electrodes, wherein said sequence of pulses form a plurality of pre-programmable waveforms available for specific clinical needs;

means to restrict said waveforms available to those appropriate for said electrode and treatment;

means for allowing a user to select and control specific waveforms and intensities of said waveforms comprising a removable tether having a first and second end wherein said first end is affixed to said electrode assembly and said second end is affixed to said miniature transcutaneous electrical neuro or muscular-stimulation unit;

means to identify said waveform, its intensity and its duration; and means for supplying power to said electronics module wherein said means for supplying power is integrated with said electrodes in one assembly.

2. The miniature transcutaneous electrical neuro or muscular-stimulation unit of claim 1 wherein said means to restrict said waveforms comprises a series of one or more electrical contacts within said housing, wherein said electrical contacts interface with said electrodes and with said electronics module to identify the type of electrode and determine the allowable waveforms that can be used.

3. The miniature transcutaneous electrical neuro or muscular-stimulation unit of claim 2 wherein said means for supplying power to said electronics module are a plurality of batteries.

4. The miniature transcutaneous electrical neuro or muscular-stimulation unit of claim 3 where said batteries are replaceable or rechargeable.

5. The miniature transcutaneous electrical neuro or muscular-stimulation unit of claim 2 wherein said electronics module applies voltage to said electrodes through said electrical contacts when said electrodes are attached to said housing.

6. The miniature transcutaneous electrical neuro-or muscular stimulation unit of claim 1 wherein said identifying means is an LCD digital readout display.

7. The miniature transcutaneous electrical neuro or muscular-stimulation unit of claim 6 wherein said means for allowing said user to select and control specific waveforms and intensities of said waveforms is through a series of input devices that interface with the said electronic module which allows the user to vary said intensity of said waveforms.

8. The miniature transcutaneous electrical neuro or muscular-stimulation unit of claim 1 wherein said electrodes are disposable.

9. The miniature transcutaneous electrical neuro or muscular-stimulation unit of claim 1 wherein said electrodes are detachable and able to be snapped into and out of each said electronic module within said housing of said miniature transcutaneous electrical neuro or muscular-stimulation unit.

10. The miniature transcutaneous electrical neuro or muscular-stimulation unit of claim 9 wherein said electrodes have integrated conducting leads, have varying shapes and sizes and can be affixed directly to a site or other area requiring electrical neuro or muscular-stimulation anywhere on said user's body, said electrodes being positioned at a specified distance from said electronics module wherein said electrodes allow for optimal placement of said electrodes at said pain site or said area requiring electrical neuro or muscular-stimulation.

11. The miniature transcutaneous electrical neuro or muscular-stimulation unit of claim 10 further comprising:

a gauze pad comprising an antibacterial agent positioned substantially adjacent to and substantially beneath said electronics module; and a plurality of adhesive strips in which said plurality of electrodes are embedded.

12. The miniature transcutaneous electrical neuro-stimulation unit of claim 11 wherein said plurality of waveforms are comprised of a conventional or modulation low mode and a microcurrent mode.

13. The miniature transcutaneous electrical neuro or muscular-stimulation unit of claim 12 wherein a conventional-low or modulation-low mode supplies to said plurality of electrodes said biphasic or monophasic pulses of about 0–60 milliamperes at a frequency of about 80–100 Hz having a pulse width of about 75 microseconds.

14. The miniature transcutaneous electrical neuro or muscular-stimulation unit of claim 12 wherein said micro current mode supplies to said plurality of electrodes said biphasic pulse of about 0–100 microamperes at a frequency of about 0.3–100 Hz.

15. The miniature transcutaneous electrical neuro-stimulation unit of claim 1 wherein said plurality of waveforms are comprised of but not limited to, a conventional-low mode and a conventional-high mode, a modulation-low mode and a modulation-high mode, an acupuncture-like low mode and an acupuncture-like high mode, a microcurrent mode, a burst mode and a cycling mode.

16. The miniature transcutaneous electrical neuro or muscular-stimulation unit of claim 15 wherein said conventional-low mode supplies to said plurality of electrodes said biphasic or monophasic pulses of about 0–60 milliamperes at a frequency of about 100 Hz having a pulse width of about 75 microseconds.

17. The miniature transcutaneous electrical neuro or muscular-stimulation unit of claim 15 wherein said conventional-high mode supplies to said electrodes said biphasic or monophasic pulses of about 0–100 milliamperes at a frequency of about 100 Hz having a pulse width of about 125 microseconds.

18. The miniature transcutaneous electrical neuro or muscular-stimulation unit of claim 15 wherein said modulation-low mode supplies to said electrodes said biphasic or monophasic pulses of about 0–60 milliamperes at a frequency of about 50–100 Hz having a pulse width of about 75–100 microseconds.

19. The miniature transcutaneous electrical neuro or muscular-stimulation unit of claim 15 wherein said modulation-high mode supplies to said electrodes said biphasic or monophasic pulses of about 0–100 milliamperes at a frequency of about 75–125 Hz having a pulse width of about 100–125 microseconds.

20. The miniature transcutaneous electrical neuro or muscular-stimulation unit of claim 15 wherein said acupuncture-like low mode supplies to said plurality of electrodes said biphasic pulses of about 0–60 milliamperes at a frequency of about 1 Hz having a pulse width of about 75 microseconds.

21. The miniature transcutaneous electrical neuro or muscular-stimulation unit of claim 15 wherein said acupuncture-like high mode supplies to said electrodes said biphasic pulses of about 0–100 milliamperes at a frequency of about 2 Hz having a pulse width of about 125 microseconds.

22. The miniature transcutaneous electrical neuro or muscular-stimulation unit of claim 15 wherein said microcurrent mode supplies to said plurality of electrodes said biphasic pulse of about 0.1–100 microamperes at a frequency of about 0.3–100 Hz.

23. The miniature transcutaneous electrical neuro or muscular-stimulation unit of claim 15 wherein said burst mode supplies to said plurality of electrodes said biphasic or monophasic pulses of about 1–100 milliamperes at a frequency of about 100 Hz having a pulse width of about 75 microseconds for a duration of three seconds on and three seconds off.

24. The miniature transcutaneous electrical neuro or muscular-stimulation unit of claim 15 wherein said cycling mode allows said user to program two or more said modes into an individualized program.

25. The miniature transcutaneous electrical neuro-stimulation unit of claim 1 wherein said plurality of waveforms are comprised of but not limited to, three unique muscle stimulation modes, a conventional mode, a modulation mode and three alternative cycling modes.

26. The miniature transcutaneous electrical neuro or muscular-stimulation unit of claim 25 wherein said first muscle stimulation mode supplies to said plurality of electrodes said biphasic or monophasic pulses typically of about 1–100 milliamperes at a frequency of about 45 Hz at a pulse width of about 300 microseconds for approximately 5 minutes on and 5 minutes off.

27. The miniature transcutaneous electrical neuro or muscular-stimulation unit of claim 25 wherein said second muscle stimulation mode supplies to said plurality of electrodes said biphasic or monophasic pulses typically of about 1–100 milliamperes at a frequency of about 45 Hz at a pulse width of about 300 microseconds for approximately 10 minutes on and 10 minutes off.

28. The miniature transcutaneous electrical neuro or muscular-stimulation unit of claim 25 wherein said third muscle stimulation mode supplies to said plurality of electrodes said biphasic or monophasic pulses typically of about 1–100 milliamperes at a frequency of about 45 Hz at a pulse width of about 300 microseconds for approximately 10 minutes on and 50 minutes off.

29. The miniature transcutaneous electrical neuro or muscular-stimulation unit of claim 25 wherein said conventional mode supplies to said plurality of electrodes said biphasic or monophasic pulses typically of about 1–100 milliamperes at a frequency of about 125 Hz at a pulse width of about 125 microseconds.

30. The miniature transcutaneous electrical neuro or muscular-stimulation unit of claim 25 wherein said modulation mode supplies to said plurality of electrodes said biphasic or monophasic pulses typically of about 0–100 milliamperes at a frequency of about 75–125 Hz at a pulse width of about 100–125 microseconds.

31. The miniature transcutaneous electrical neuro or muscular-stimulation unit of claim 25 wherein said first alternative cycling mode supplies to said plurality of electrodes a sequence of said biphasic or monophasic pulses comprised of said modulation mode for about 3 minutes followed by said first muscle stimulation mode for about 9 minutes, followed by said modulation for about 3 minutes.

32. The miniature transcutaneous electrical neuro or muscular-stimulation unit of claim 25 wherein said second alternative cycling mode supplies to said plurality of electrodes a sequence of said biphasic or monophasic pulses comprised of said modulation mode for about 3 minutes followed by said first muscle stimulation mode for about 9 minutes, followed by said modulation mode for about 3 minutes.

33. The miniature transcutaneous electrical neuro or muscular-stimulation unit of claim 25 wherein said third alternative cycling mode supplies to said plurality of electrodes a sequence of said biphasic or monophasic pulses comprised of said modulation mode for about 3 minutes followed by said third muscle stimulation mode for about 9 minutes, followed by said modulation mode for about 3 minutes.

34. A method of relieving acute or chronic body pain or muscle dysfunction requiring electrical neuro or muscular-stimulation on a user's body using the miniature transcutaneous electrical neuro or muscular-stimulation unit of claim 1 comprising the steps of:

affixing a plurality of electrodes to a treatment site or other area requiring electrical neuro or muscular-stimulation on a user's body;

applying said biphasic or monophasic sequence of pulses to said electrodes via an electrical circuit;

providing a means for said user to select and control said plurality of waveforms and intensity of said waveforms;

providing a means for said user to identify said waveform, its intensity and its duration; and providing a means for supplying power to said electronics module wherein said means for supplying power is integrated with said electrodes in one detachable assembly.

35. The miniature transcutaneous electrical neuro or muscular-stimulation unit of claim 1 further comprising:

a remote controller wherein said controller includes a transmitting device with means to transmit signals denoting the desired waveform mode to said miniature transcutaneous electrical neuro-stimulation unit by a communication means; and means within said electronics module for receiving and decoding said signals from said transmitting device and generating said desired waveforms.

36. The miniature transcutaneous electrical neuro or muscular-stimulation unit of claim 35 wherein said communication means is achieved by capacitive coupling comprised of a plurality of conductive plates or transducers placed near the surface of said user's skin wherein one of said conductive plates or transducers resides in said remote controller and the other said conductive plate or transducer resides in said miniature transcutaneous electrical neuro or muscular-stimulation unit, using the user's body as a conductive medium to transmit said signals.

37. The miniature transcutaneous electrical neuro or muscular-stimulation unit of claim 35 wherein said remote controller transmits said signals at a frequency of between 20–500 kHz from said remote controller through the user's body to said transcutaneous electrical neuro-stimulation unit.

38. The miniature transcutaneous electrical neuro or muscular-stimulation unit of claim 35 wherein said communication means is achieved by over-the-air RF transmission in the frequency range of 40 kHz to 915 MHz.

39. The miniature transcutaneous electrical neuro or muscular-stimulation unit of claim 35 wherein said transmission signals are synchronized to said miniature transcutaneous electrical neuro or muscular-stimulation unit's said monophasic or biphasic sequence of pulses to avoid interference of said transmission signals with said monophasic or biphasic sequence of pulses.

40. The miniature transcutaneous electrical neuro or muscular-stimulation unit of claim 35 further comprising a means of synchronizing separate electrodes such that their polarities are 180 degrees out of phase.

41. The miniature transcutaneous electrical neuro or muscular-stimulation unit of claim 35 wherein said remote controller is adapted to be worn on said user's wrist.

42. The miniature transcutaneous electrical neuro or muscular-stimulation unit of claim 35 where said electronics module is a remote module with display means which allows said remote module to be identified by said remote controller and which sets a software address thereby allowing said remote controller to send said signals to said identified remote module.

43. The miniature transcutaneous electrical neuro or muscular-stimulation unit of claim 1 further comprising:

a standard splint, bandage, manufactured brace, or cast comprised of multiple layers;

said splint, bandage, brace or cast embedded with non-visible wires or flex-circuit material;

said electrodes are embedded in said splint, bandage, brace, or cast;

said wires or flex-circuit material to provide for connection between said plurality of electrodes and disposable said miniaturized transcutaneous electrical neuro-or muscular stimulation unit; and said plurality of electrodes arranged in a grid-like manner to allow for programming of a specific firing order which can provide for greater therapeutic effect to said pain site.

44. The miniature transcutaneous electrical neuro or muscular-stimulation unit of claim 35 further comprising:

a standard splint, bandage, manufactured brace, or cast comprised of multiple layers;

said splint, bandage, brace or cast embedded with non-visible wires or flex-circuit material;

said electrodes are embedded in said splint, bandage, brace, or cast;

said wires or flex-circuit material to provide for connection between said plurality of electrodes and disposable said miniaturized transcutaneous electrical neuro-or muscular stimulation unit; and said plurality of electrodes arranged in a grid-like manner to allow for programming of a specific firing order which can provide for greater therapeutic effect to said pain site.

45. The miniature transcutaneous electrical neuro or muscular-stimulation unit of claim 35 wherein said remote controller is adapted to be worn about said user's neck as a pendant.

46. The miniature transcutaneous electrical neuro or muscular-stimulation unit of claim 1 wherein said means for supplying power is integrated with said electrodes in one assembly.

47. The miniature transcutaneous electrical neuro or muscular-stimulation unit of claim 1 wherein said means for supplying power comprises at least one battery positioned in a battery housing within said housing.

* * * * *